(12) United States Patent
da Costa e Silva et al.

(10) Patent No.: US 6,710,229 B2
(45) Date of Patent: Mar. 23, 2004

(54) CELL CYCLE STRESS-RELATED PROTEINS AND METHODS OF USE IN PLANTS

(75) Inventors: Oswaldo da Costa e Silva, Apex, NC (US); Hans J. Bohnert, Tucson, AZ (US); Nocha van Thielen, Cary, NC (US); Rouying Chen, Apex, NC (US); Rodrigo Sarria-Millan, Morrisville, NC (US)

(73) Assignee: BASF Plant Science GmbH, Ludwigshafen (DE)

( * ) Notice: Subject to any disclaimer, the term of this patent is extended or adjusted under 35 U.S.C. 154(b) by 0 days.

(21) Appl. No.: 09/828,062

(22) Filed: Apr. 6, 2001

(65) Prior Publication Data

US 2003/0097675 A1 May 22, 2003

Related U.S. Application Data

(60) Provisional application No. 60/196,001, filed on Apr. 7, 2000.

(51) Int. Cl.$^7$ .......................... C12N 15/29; C12N 15/82; A01H 5/00; A01H 5/10
(52) U.S. Cl. ..................... 800/289; 800/298; 536/23.6; 435/320.1; 435/419
(58) Field of Search .................... 435/320.1, 419, 435/468; 536/23.6; 800/289, 298

(56) References Cited

FOREIGN PATENT DOCUMENTS

| WO | WO 99/54489 A1 | 10/1999 |
|----|----------------|---------|
| WO | WO 00/36124 A2 | 6/2000  |

OTHER PUBLICATIONS

Espinosa–Ruiz et al., *Arabisdopsis thaliana AtHAL3: a flavoprotein related to salt and osmotic tolerance and plant growth*, The Plant Journal, 1999 20(5), pp. 529–539.

Machuka et al., *Sequence analysis of Expressed Sequence Tags from an ABA–Treated cDNA Library Identifies Stress Response Genes in the Moss Physcomitrella patens*, Plant Cell Physiol., 1999 40(4), pp. 378–387.

Reski, Ralf, *Molecular genetics of Physocomitrella*, Planta, Springer Verlag, May 1999, pp. 301–309.

Rounsley et al., *Putative SKD 1 Protein (F10A12.27/ F10A12.27)*, Accession No. Q9ZNTO, pp. 1–2.

Feiler, H.S. et al., "The Higher Plant *Arabidopsis thaliana* Encodes a Functional CDC48 Homologue Which is Highly Expressed in Dividing and Expanding Cells", The EMBO Journal, 14:5626–5637; 1995.

Schuppler, U. et al., "Effect of Water Stress on Cell Division and Cell–Division–Cycle–2–Like Cell–Cycle Kinase Activity in Wheat Leaves", Plant Physiol., 117:667–678, 1998.

Tardieu, F. and Granier, C. "Quantitative Analysis of Cell Division in Leaves: Methods, Developmental Patterns and Effects of Environmental Conditions", Plant Molecular Biology, 43:555–567, 2000.

Van't Hof, J., "The Regulation of Cell Division in Higher Plants", Basic Mechanisms in Plant Morphogenesis, 25:152–165, 1974.

*Primary Examiner*—Phuong T. Bui
*Assistant Examiner*—Cynthia Collins
(74) *Attorney, Agent, or Firm*—Sutherland Asbill & Brennan LLP

(57) ABSTRACT

A transgenic plant transformed by a Cell Cycle Stress-Related Protein (CCSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated CCSRPs, and isolated nucleic acid coding CCSRPs, and vectors and host cells containing the latter.

18 Claims, 19 Drawing Sheets

FIGURE 1A

Nucleotide sequence of the partial CC-1 from *Physcomitrella patens* (SEQ ID NO:1)

CGGGAGTTGGTGATCTTCAGCATGCTCGTAGTTGACAAGGGAGGTAGGATTGTTTGA

CCCAAGGTGTGTANAGAAGGGGATAGCCATGTACAGCAACTTCAAAGAGCAGGCCA

TAGAATATTGTGCGTCAAGCCGTAGCGGAAGACAACGCAGGGAACTATGCCAAAGC

GTTTCCGCTGTACATGAACGCGCTTGAGTACTTCAAGACGCATCTAAAGTATGAGAA

GAATCCCAAAATCAAGGAGGCCATCACTCAGAAGTTCACGGAGTATTTGAGGAGGG

CGGAGGAGATTCGAGCCGTTTTGGACGATGGCCCCACTGGACCCTCTGCAAATGGA

GACGCGGCAGTTCAAGCTAAACCGAAGTCGAAATCAGGGAAGAAGGATGGTGGCG

GGGGTGATGGTGATGGTGACAGCGAGGATCCCGACCAGCAGAAGCTGAGATCAGGG

CTGAACTCGGCAATCATACGGGAAAAGCCAAATGTTCGGTGGGCTGATGTTGCTGG

ACTTGAAAGTGCCAAGCAGGCGTTGCAGGAGGCAGTGATCTTGCCCGTGAAGTTTCC

CCAATTTTTCACAGGGAAGCGAAGAACATGGCGAGCATTTTGTGGTATGGGCCCCC

CGGGACTGGAAAATCGTATCTTGCAAAAGCTGTTGCTACGGAAGCTGATTCTACATT

CTTTAGTATTTCCTCTTCAGACTTGGTGTCAAAGTGGATGGGAGAGAGTGAGAAGCT

TGTTGCAAATCTGTTTCAAATGGCCCGTGAAGCTGCTCCATCCATCATCTTCATAGAC

GAGATTGATTCTTTATGCGGTACTCGAGGTGAAGGAAATGAGAGCGAGGCTTCACG

TCGTATCAAGACTGAGTTGCTAGTTCAAATGCAGGGTGTC

FIGURE 1B

Nucleotide sequence of the partial CC-2 from *Physcomitrella patens* (SEQ ID NO:2)

CGGCACCAGGGAGATCGTATTGAGGTAACAGGAGTTTTCAAGGCCATGGCAGTTCG

AGTTGGTCCGAATCAACGAACATTACGAGCATTGTATAAGACCTACATCGATTGCGT

GCACGTCAAGAAGTCTGACAGGGGTCGACTGCAAACTGAAGATCCTATGGAGATGG

ATAAGGAGAATGATATGTATGCTGGGTATCATGAAAGTGATACTTCAGAAGCTGCT

AATGAAGCAAAGATTCAAAAACTTAAAGAGCTGTCCAAGCTCCCGGACATTTATGA

TAGACTTTCAAGGTCGCTGGCTCCAAGCATTTGGGAGCTTGAAGATATTAAAAAGGG

TCTTCTTTGCCAGCTCTTTGGTGGGAAGGCTAAGAAAATTCCATCTGGAGCATCTTTC

CGAGGTGACATCAATGTTTTACTTGTTGGGGACCCTGGTACCAGTAAATCTCAGCTG

CTTCAGTATGTGCACAAGATAGCTCCTCGTGGAATCTACACTAGTGGGCGAGGAAGT

TCGGCGGTTGGGCTGACAGCGTATGTAAACGAAGGATCCAGAAACTCGAGAGACGG

TATTGGAGAGCGGAGCTTTGGTTCTTAGTGATCGTGGGATATGCTGTATCGATGAGT

TCGACAAAATGTCTGATAATGCCCGAAGCATGCTTCATGAGGTAATGGAGCAACAA

ACGGTATCTGGACCCAAGCGGTTCATGCTCGTGAAGCCGAGTTG

FIGURE 1C

Nucleotide sequence of the partial CC-3 from *Physcomitrella patens* (SEQ ID NO:3)

GCACCAGCCGCTTTGGAATCCCATCCCTCGGTTGCATAGACACAAGGGGATTCAGTG

TAGTGATACGTTGTGCATATTTGGTGTTGCAAGATTTTTGGTTTCTTGATTGTTAGCT

ATGGCGTCTGCAACAGCGGCTACAATGGCGTCCCTCCTCACGCCTGGGTCTCTCCGA

CGCGGTTTGGGTAGCCAGGAATCGTCGACCCAATTTGCTCCCCTAGCTGGTCCTCGT

AAGACATCAGTTTCGCGTAGGGTGACTGCTAGCGCTAGTGGGAAGAACGACAATGG

AGTCGTGGAAGATGTGGATATGGGGAAGCGGGGTATGTTGAAAGGCGTAGCGGGAG

CTTTGGCTGCAGTTCTCCCTGCTGTTATCGCGAAGAAAGCTTCAGCAGCTGAGGAGC

AGGGCGTAGCGTCTTCCAGGATGTCCTACTCGAGGTTTTGGAGTATTTGGATATGG

ACCGTGTGAAGAAGTTGACTTGTATGAAAATGGGACCATAGCAATTGTGGAGGCTG

TATCCCCTGAATTGGGCAACAGAGTGCAACGCGTACGCGTGCAGCTCCCCGGAAC

FIGURE 2A

Nucleotide sequence of the full-length CC-1 from *Physcomitrella patens* (SEQ ID NO:4)

GCGATATCGACCCAAGGTGTGTAGAGAAGGGGATAGCCATGTACAGCAACTTCAAA

GAGCAGGCCATAGAATATGTGCGTCAAGCCGTAGCGGAAGACAACGCAGGGAACTA

TGCCAAAGCGTTTCCGCTGTACATGAACGCGCTTGAGTACTTCAAGACGCATCTAAA

GTATGAAGAATCCCAAAATCAAGGAGGCCATCACTCAGAAGTTCACGGAGTATT

TGAGGAGGGCGGAGGAGATTCGAGCCGTTTTGGACGATGGCCCCACTGGACCCTCT

GCAAATGGAGACGCGGCAGTTCAAGCTAAACCGAAGTCGAAATCAGGGAAGAAGG

ATGGTGGCGGGGGTGATGGTGATGGTGACAGCGAGGATCCCGAGCAGCAGAAGCTG

AGATCAGGGCTGAACTCGGCAATCATACGGGAAAAGCCAAATGTTCGGTGGGCTGA

TGTTGCTGGACTTGAAAGTGCCAAGCAGGCGTTGCAGGAGGCAGTGATCTTGCCCGT

GAAGTTTCCCCAATTTTTCACAGGGAAGCGAAGACCATGGCGAGCATTTTGTTGTA

TGGGCCCCCCGGGACTGGAAAATCGTATCTTGCAAAAGCTGTTGCTACGGAAGCTG

ATTCTACATTCTTTAGTATTTCCTCTTCAGACTTGGTGTCAAAGTGGATGGGAGAGA

GTGAGAAGCTTGTTGCAAATCTGTTTCAAATGGCCCGTGAAGCTGCTCCATCCATCA

TCTTCATAGACGAGATTGATTCTTTATGCGGTACTCGAGGTGAAGGAAATGAGAGCG

AGGCTTCACGTCGTATCAAGACTGAGTTGCTAGTTCAAATGCAGGGTGTCGGCAATC

AAGACACTAAGGTTCTTGTGTTAGCTGCTACAAATACGCCCTACTCTTTGGATCAGG

CGGTGAGGCGACGTTTCGACAAGCGTATCTACATCCCACTACCGGAGTCTAAGGCTC

GGCAGCACATGTTTAAGGTGCATTTGGGAGATACGCCAAACAACCTGACTGAACGT

GATTATGAGGATCTGGCTAGGAAGACTGATGGGTTTTCAGGCTCGGATATTGCAGTT

TGTGTGAAAGATGTACTATTTGAGCCTGTTCGTAAGACCCAAGATGCTATGCATTTC

AAAAGAATTAATACCAAAGAAGGAGAGATGTGGATGCCTTGTGGGCCCCGAGAACC

FIGURE 2A (Continued)

AGGTGCTAGGCAAACCACTATGACGGAGCTTGCCGCTGAAGGGCAGGCATCGAAGA

TTTTACCACCTCCAATCACAAAATCAGATTTCGACAAAGTCCTCGCAAAGCAGAGGC

CCACTGTCAGCAAAGGCGACCTTATTATTCAAGAGAAATTCACCAAAGAATTTGGTG

AAGAAGGTTGAATGGTGCTTCGAGTTAAGAATTTGGAAGGTTCTGGGTTACGGAAG

ACAGACGAAATAGAACGTCGTAGGTACGGTAGCCTAAGAGTAAATTACGGAAGTTT

TCCGACTTGCCAGTTGTGCACTCTTTCAACATGAAGGGAAGGAAGCTACTTGTCGGT

TGCCTTTTCATGGGTGAGTTGCATCAGTCGCGAGCTCGC

FIGURE 2B

Nucleotide sequence of the full-length CC-2 from *Physcomitrella patens* (SEQ ID NO:5)

ATGGCGCCGCACTCACGTGAGGAATTGCACCTCCTTGTTCTGCGACGGTTCCATT

CTTTTGGTTTTTAGTTTGCAAATCTTGATCGTGGAGTTGAGAAAAGGGCGGTTCGT

TGTCTTGAGGTGTTCTTGTTGATTGTTCGTCATGGAAAATAATGATGCACTTGACATT

GGAGCCGTGTCGTCCCATATCCTTCGCAATCTGAAGGAGTGTCTACGCCATTGCCG

CAAGTAACATCACCGAGCTTCGACAATGCAGCCTCACCCGTGGCCGGGCGGAGGGC

CGTACGGCAGACCCCTACATCTGCAGTTCGAAGGAGAGGGAGAGAAACGGATTCCG

CTCGTCGTAGGAGGAGTCGATCTCGCAGTTTAGGCAATTCTGTTTATAGTTCCCCTTA

CGATGCGGGGACTCCTGGAACTCCTGGAACTCCAGTGGCTACTCCGGTTTACGCTAC

CCCAGTCGGTACACCTATGGGTACCCCATCGTTCATCGTGGCACGCCACAGTACAA

ACAGCGCAGTGAGCTTGGTTCCCAGGGGAAGCCTCTACATCGGAGACGTCGATCTC

AATCCAGAGAACCCGGGCATCGATCTCCTTCAAGGGAACCTAGTGCTGATGGGCGT

CCCTCTGAATCTGCTGAGCCAGATGACACTTGGGTGGAGAATATGCTTATGTTTGG

GGGACGAATGTTAACATTCCAGATGTGCTTAGGGCGATTCGTCGATTTCTCCACAAT

TATCGTTCGAGTGCTCATGATCTTAATTCCAAGTACATCCAGATCATAGAGGAGACT

GTGGAGCGTGAGGAGGATACTCTAAATATCGACATGTCAGACATTTATGACCATGAT

CCTGATCTATACGCAAAAATTGTTCGATACCACTCGACATCATCCCCCTGTTGGAC

ACTGAGTGTCAGGAAGTTGCTACCTCTTTACTACCAACGTTTGAGAAGCATATTGAG

GCCAGACCTTTCAATCTCAAAGCATCGGTGCACATGCGTGAACTCAACCCTTCAGAT

ATAGACAAATTGGTTTCTGTTAAAGGAATGGTTATCCGGTGCAGTTCTATCATACCT

GAAATTAAGGGGGCCTTCTTCAAATGTTTAGTGTGTGGTCACTCGCCTCCGCTAGTT

ACAGTTGTTAAAGGGCGGGTTGAGGAGCCAACAAGGTGTGAAAAGCCAGAATGTGC

FIGURE 2B (Continued)

```
AGCACGGAATGCTATGTCTCTTATTCACAATCGATGCACTTTTGCAAATAAGCAGAT
AGTGCGTCTTCAAGAAACTCCAGATGCCATTCCTGAAGGAGAGACTCCACACACAG
TCAGCATGTGTTTATACAACACTATGGTTGATGCTGTGAAGCCTGGAGATCGTATTG
AGGTAACAGGAGTTTTCAAGGCCATGGCAGTTCGAGTTGGTCATGGCGCGCCGCACT
CACGTGAGGAATTGCACCTCCTTGTTCTGCGACGGTTCCATTCTTTTGGTTTTTAGT
TTGCAAATCTTGATCGTGGAGTTGAGAAAAAGGGCGGTTCGTTGTCTTGAGGTGTTC
TTGTTGATTGTTCGTCATGGAAAATAATGATGCACTTGACATTGGAGCCGTGTCGTC
CCCATATCCTTCGCAATCTGAAGGAGTGTCTACGCCATTGCCGCAAGTAACATCACC
GAGCTTCGACAATGCAGCCTCACCCGTGGCCGGGCGGAGGGCCGTACGGCAGACCC
CTACATCTGCAGTTCGAAGGAGAGGGAGAGAAACGGATTCCGCTCGTCGTAGGAGG
AGTCGATCTCGCAGTTTAGGCAATTCTGTTTATAGTTCCCCTTACGATGCGGGGACTC
CTGGAACTCCTGGAACTCCAGTGGCTACTCCGGTTTACGCTACCCCAGTCGGTACAC
CTATGGGTACCCCATCGTTCCATCGTGGCACGCCACAGTACAAACAGCGCAGTGAG
CTTGGTTCCCAGGGGAAGCCTCTACATCGGAGACGTCGATCTCAATCCAGAGAACCC
GGGCATCGATCTCCTTCAAGGGAACCTAGTGCTGATGGGCGTCCCTCTGAATCTGCT
GAGCCAGATGACACTTTGGGTGGAGAATATGCTTATGTTTGGGGGACGAATGTTAAC
ATTCCAGATGTGCTTAGGGCGATTCGTCGATTTCTCCACAATTATCGTTCGAGTGCTC
ATGATCTTAATTCCAAGTACATCCAGATCATAGAGGAGACTGTGGAGCGTGAGGAG
GATACTCTAAATATCGACATGTCAGACATTTATGACCATGATCCTGATCTATACGCA
AAAATTGTTCGATACCCACTCGACATCATCCCCCTGTTGGACACTGAGTGTCAGGAA
GTTGCTACCTCTTTACTACCAACGTTTGAGAAGCATATTGAGGCCAGACCTTTCAAT
CTCAAAGCATCGGTGCACATGCGTGAACTCAACCCTTCAGATATAGACAAATTGGTT
```

FIGURE 2B (Continued)

TCTGTTAAAGGAATGGTTATCCGGTGCAGTTCTATCATACCTGAAATTAAGGGGGCC

TTCTTCAAATGTTTAGTGTGTGGTCACTCGCCTCCGCTAGTTACAGTTGTTAAAGGGC

GGGTTGAGGAGCCAACAAGGTGTGAAAAGCCAGAATGTGCAGCACGGAATGCTATG

TCTCTTATTCACAATCGATGCACTTTTGCAAATAAGCAGATAGTGCGTCTTCAAGAA

ACTCCAGATGCCATTCCTGAAGGAGAGACTCCACACACAGTCAGCATGTGTTTATAC

AACACTATGGTTGATGCTGTGAAGCCTGGAGATCGTATTGAGGTAACAGGAGTTTTC

AAGGCCATGGCAGTTCGAGTTGGTCCGAATCAACGAACATTACGAGCATTGTATAA

GACCTACATCGATTGCGTGCACGTCAAGAAGTCTGACAGGGGTCGACTGCAAACTG

AAGATCCTATGGAGATGGATAAGGAGAATGATATGTATGCTGGGTATCATGAAAGT

GATACTTCAGAAGCTGCTAATGAAGCAAAGATTCAAAAACTTAAAGAGCTGTCCAA

GCTCCCGGGCATTTATGATAGACTTTCAAGGTCGCTGGCTCCAAGCATTTGGGAGCT

TGAAGATATTAAAAAGGGTCTTCTTTGCCAGCTCTTTGGTGGGAAGGCTAAGAAAAT

TCCATCTGGAGCATCTTTCCGAGGTGACATCAATGTTTTACTTGTTGGGGACCCTGGT

ACCAGTAAATCTCAGCTGCTTCAGTATGTGCACAAGATAGCTCCTCGTGGAATCTAC

ACTAGTGGGCGAGGAAGTTCGGCGGTTGGGCTGACAGCGTATGTAACGAAGGATCC

AGAAACTCGAGAGACGGTATTGGAGAGCGGAGCTTTGGTTCTTAGTGATCGTGGGA

TATGCTGTATCGATGAGTTCGACAAAATGTCTGATAATGCCCGAAGCATGCTTCATG

AGGTAATGGAGCAACAAACGGTATCTGTAGCCAAAGGGGGTATCATTGCCTCGCTG

AACGCTCGGACGTCTGTCCTTGCATGTGCAAATCCTAGTGGGTCCCGATACAATGCG

CGCCTTTCTGTGATTGATAACATCCAGCTTCCTCCAACTCTACTTTCTAGATTTGATT

TAATTTACTTAATGCTCGACAAACCAGACGAGCAAAACGATCGTCGTCTCGCCAGGC

ATCTCGTGGCTTTACACTATGAAAACTATGAAGTTTCAAAGCAGGACGCCTTAGATC

FIGURE 2B (Continued)

```
TACAAACACTTACCGCGTATATCACCTATGCTCGTCAGCATGTACATCCTACATTAA
GTGATGAAGCTGCTGAAGATTTGATTAATGGCTATGTTGAGATGCGCCAAAAGGGC
AACTTTCCTGGAAGCAGTAAAAAGGTGATAACAGCCACACCTCGGCAACTCGAAAG
TATGATTCGTATCAGTGAAGCCCTAGCTCGAATGAGATTTTCTGAAGTGGTAGAGAA
AGTTGATGCAGCAGAAGCTGTGCGCCTTTTAGACGTCGCTTTGCAGCAATCTGCTAC
TGATCATGCAACAGGTACGATAGACATGGATCTTATCACGACTGGAGTGTCGGCCA
GCGAGCGTATTCGTCGGGCCAACTTGCTAGCTGCTCTGCGAGAGCTTATAGCAGATA
AAATTTCACCTGGCAGCTCCTCTGGCTTGAAGACCAGTCAGCTTCTTGAGGATATCC
GGAGCCAAAGCAGTGTGGACGTTAGTTTGCAGGATATTAAAAATGCTCTGGGTAGC
CTCCAAGGAGAAGGCTTTCTTACTGTCCATGGTGACATAGTCAAGAGAGTTTGAGAC
AGTTTCTAACTGTTCGAATCCATGAGCTATAACTCTGAACGAAAGGGAAAACCTCCA
GTTTCCCATGCGCAATTCCCAGAGCTCGC
```

FIGURE 2C

Nucleotide sequence of the full-length CC-3 from *Physcomitrella patens* (SEQ ID NO:6)

ATCCCGGGTGATACGTTGTGCATATTTGGTGTTGCAAGTTTTTGGTTTCTTGATTGT
TAGCTATGGCGTCTGCAACAGCGGCTACAATGGCGTCCCTCCTCACGCCTGGGTCTC
TCCGACGCGGTTTGGGTAGCCAGGAATCGTCGACCCAATTTGCTCCCCTAGCTGGTC
CTCGTAAGACATCAGTTTCGCGTAGGGTGACTGCTAGCGCTAGTGGGAAGAACGAC
AATGGAGTCGTGGAAGATGTGGATATGGGGAAGCGGGGTATGTTGAAAGGCGTAGC
GGGAGCTTTGGCTGCAGTTCTCCCTGCTGTTATCGCGAAGAAAGCTTCAGCAGCTGA
GGAGCAGGGCGTAGCGTCTTCCAGGATGTCCTACTCGAGGTTTTTGGAGTATTTGGA
TATGGACCGTGTGAAGAAGGTTGACTTGTATGAAAATGGGACCATAGCAATTGTGG
AGGCTGTATCCCCTGAATTGGGCAACAGAGTACAACGCGTACGCGTGCAGCTCCCC
GGAACTAGCTCCGAATTGTTGTCGAAGTTTAGATCGAAGAATGTAGATTTTGCCGCA
CACAGCCCACAAGAGGACTCTGGCTCTGTCATTTTGAACCTCATCGGAAATTTGGCT
TTCCCCTTGTTGCTCGTTGGAGGTCTGTTCTTCTTGTCTCGTAGATCCCAAGGTGGTA
TGGGACCTGGCGGTCCTGGGAACCCGATGGCCTTCGGGAAGTCCAAGGCCAAGTTC
CAGATGGAGCCCAACACGGGCATTACATTCCAAGATGTTGCGGGAGTAGACGAGGC
CAAGCAAGACTTCATGGAGGTTGTGGAGTTCTTGAAGCGGCCTGAGAGATTCACAG
CAGTGGGCGCTAAAATCCCAAGGGAGTGTTGCTGGTTGGACCACCCGGTACCGGA
AAGACTCTATTGGCGAAGGCCATCGCTGGGGAAGCTGGAGTACCATTCTTCTCCATC
TCTGGGTCTGAGTTCGTGGAAATGTTCGTGGGAGTGGGAGCTTCCCGTGTGAGGGAC
TTGTTCAAGAAGGCGAAAGAGAATGCTCCCTGCATTGTGTTTGTGGATGAGATTGAT
GCCGTTGGAAGACAGAGAGGAACTGGAATTGGAGGAGGCAATGATGAGCGTGAGC
AGACGTTGAATCAGTTGTTGACGGAGATGGACGGTTTCGAAGGAAACACTGGTGTG

FIGURE 2C (Continued)

ATTGTCATTGCTGCCACCAACAGGGCTGATATTCTCGACGCTGCCTTGCTTCGTCCTG

GAAGATTCGACAGACAGGTTTCCGTGGATGTTCCGGACGTGAAGGGAAGGACTGAC

ATCCTCAAGGTGCATGCTAGTAACAAGAAGTTCGCCGATGATGTGTCTCTGGATATC

ATTGCCATGAGGACACCAGGGTTCAGTGGAGCTGACTTGGCCAACTTGTTGAACGA

AGCAGCTATCTTGACCGGAAGGAGAGGAAAGACAGCCATCAGTGCTAAGGAGATTG

ACGATTCAATTGACAGAATCGTTGCCGGGATGGAAGGTACCGTCATGACGGACGGC

AAGAGCAAGAGTCTTGTTGCATACCACGAAGTCGGCCATGCTATCTGCGGGACTTTG

ACTCCCGGACACGACGCCGTGCAAAAGGTCACCCTCATTCCTAGAGGTCAGGCCCG

TGGTCTCACCTGGTTTATTCCCGGAGAAGACCCGACTTTGATTTCAAAGCAGCAAAT

CTTTGCCCGTATTGTTGGTGCTCTTGGTGGTAGGGCTACCGAGCAGGTTGTCTTCGGT

GATGCTGAAGTTACGACTGGAGCGTCCAGTGATTTGCAGCAAGTTACTTCTATGGCC

AAGCAGATGGTCACAGTATTCGGTATGTCAGACATCGGCCCATGGGCTTTGATGGAC

CCTTCATCCCAGGGAGGAGATATGATTATGCGTATGATGGCACGTAACTCCATGTCC

GAGAAGTTGGCTGAGGACATCGACAAGGCTGTGAAGGCTATCTCTGACGAGGCCTA

CGAAGTCGCACTGGGTCACATTAGGAACAACCGCACGGCCATGGACAAGATTGTAG

AGGTTCTGCTTGAGAAGGAGACTTTGTCCGGCGCCGAGTTTAGGGCTATTCTTTCGG

AATACACAGAGATTCCTGCTGAAAACCGTGTATCAGACAACCAGGCCGCACCTGTA

GCTGTTTGAAGTGATCAGAAGCAAGGGTGTTTGTGAACACAATCGTGTAGGTTTTGG

AGCATCGACGCTCTTGTATCAGAGCTCGC

FIGURE 3A

Deduced amino acid sequence of CC-1 from *Physcomitrella patens* (SEQ ID NO:7)

MYSNFKEQAIEYVRQAVAEDNAGNYAKAFPLYMNALEYFKTHLKYEKNPKIKEAITQK

FTEYLRRAEEIRAVLDDGPTGPSANGDAAVQAKPKSKSGKKDGGGGDGDGDSEDPEQQ

KLRSGLNSAIIREKPNVRWADVAGLESAKQALQEAVILPVKFPQFFTGKRRPWRAFLLY

GPPGTGKSYLAKAVATEADSTFFSISSSDLVSKWMGESEKLVANLFQMAREAAPSIIFID

EIDSLCGTRGEGNESEASRRIKTELLVQMQGVGNQDTKVLVLAATNTPYSLDQAVRRRF

DKRIYIPLPESKARQHMFKVHLGDTPNNLTERDYEDLARKTDGFSGSDIAVCVKDVLFE

PVRKTQDAMHFKRINTKEGEMWMPCGPREPGARQTTMTELAAEGQASKILPPPITKSDF

DKVLAKQRPTVSKGDLIIQEKFTKEFGEEG*

FIGURE 3B

Deduced amino acid sequence of CC-2 from *Physcomitrella patens* (SEQ ID NO:8)

MENNDALDIGAVSSPYPSQSEGVSTPLPQVTSPSFDNAASPVAGRRAVRQTPTSAVRRR

GRETDSARRRRSRSRSLGNSVYSSPYDAGTPGTPGTPVATPVYATPVGTPMGTPSFHRG

TPQYKQRSELGSQGKPLHRRRRSQSREPGHRSPSREPSADGRPSESAEPDDTLGGEYAYV

WGTNVNIPDVLRAIRRFLHNYRSSAHDLNSKYIQIIEETVEREEDTLNIDMSDIYDHDPDL

YAKIVRYPLDIIPLLDTECQEVATSLLPTFEKHIEARPFNLKASVHMRELNPSDIDKLVSV

KGMVIRCSSIIPEIKGAFFKCLVCGHSPPLVTVVKGRVEEPTRCEKPECAARNAMSLIHNR

CTFANKQIVRLQETPDAIPEGETPHTVSMCLYNTMVDAVKPGDRIEVTGVFKAMAVRV

GPNQRTLRALYKTYIDCVHVKKSDRGRLQTEDPMEMDKENDMYAGYHESDTSEAANE

AKIQKLKELSKLPGIYDRLSRSLAPSIWELEDIKKGLLCQLFGGKAKKIPSGASFRGDINV

LLVGDPGTSKSQLLQYVHKIAPRGIYTSGRGSSAVGLTAYVTKDPETRETVLESGALVLS

DRGICCIDEFDKMSDNARSMLHEVMEQQTVSVAKGGIIASLNARTSVLACANPSGSRYN

ARLSVIDNIQLPPTLLSRFDLIYLMLDKPDEQNDRRLARHLVALHYENYEVSKQDALDL

QTLTAYITYARQHVHPTLSDEAAEDLINGYVEMRQKGNFPGSSKKVITATPRQLESMIRI

SEALARMRFSEVVEKVDAAEAVRLLDVALQQSATDHATGTIDMDLITTGVSASERIRRA

NLLAALRELIADKISPGSSSGLKTSQLLEDIRSQSSVDVSLQDIKNALGSLQGEGFLTVHG

DIVKRV*

FIGURE 3C

Deduced amino acid sequence of CC-3 from *Physcomitrella patens* (SEQ ID NO:9)

MASATAATMASLLTPGSLRRGLGSQESSTQFAPLAGPRKTSVSRRVTASASGKNDNGV

VEDVDMGKRGMLKGVAGALAAVLPAVIAKKASAAEEQGVASSRMSYSRFLEYLDMD

RVKKVDLYENGTIAIVEAVSPELGNRVQRVRVQLPGTSSELLSKFRSKNVDFAAHSPQE

DSGSVILNLIGNLAFPLLLVGGLFFLSRRSQGGMGPGGPGNPMAFGKSKAKFQMEPNTGI

TFQDVAGVDEAKQDFMEVVEFLKRPERFTAVGAKIPKGVLLVGPPGTGKTLLAKAIAGE

AGVPFFSISGSEFVEMFVGVGASRVRDLFKKAKENAPCIVFVDEIDAVGRQRGTGIGGG

NDEREQTLNQLLTEMDGFEGNTGVIVIAATNRADILDAALLRPGRFDRQVSVDVPDVKG

RTDILKVHASNKKFADDVSLDIIAMRTPGFSGADLANLLNEAAILTGRRGKTAISAKEID

DSIDRIVAGMEGTVMTDGKSKSLVAYHEVGHAICGTLTPGHDAVQKVTLIPRGQARGLT

WFIPGEDPTLISKQQIFARIVGALGGRATEQVVFGDAEVTTGASSDLQQVTSMAKQMVT

VFGMSDIGPWALMDPSSQGGDMIMRMMARNSMSEKLAEDIDKAVKAISDEAYEVALG

HIRNNRTAMDKIVEVLLEKETLSGAEFRAILSEYTEIPAENRVSDNQAAPVAV*

Figure 5
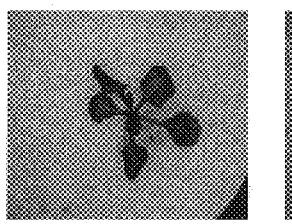 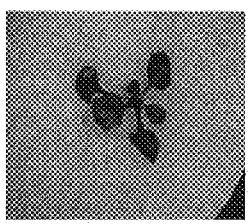 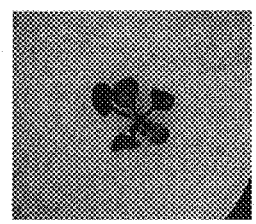
PpCC-1
Drought
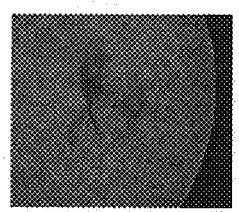 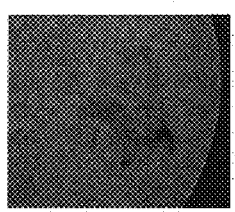 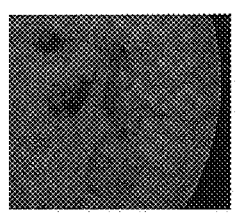
Control
Drought Figure 6
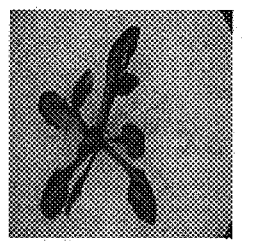 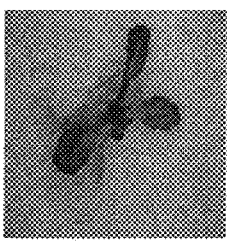 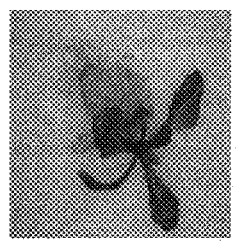 PpCC-1 Freezing
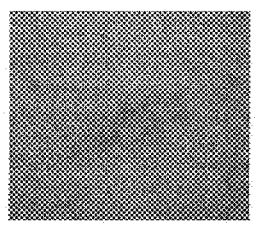 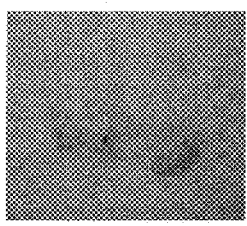 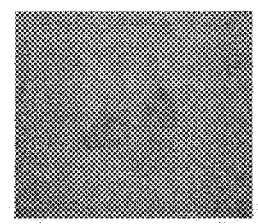 Control Freezing Figure 7
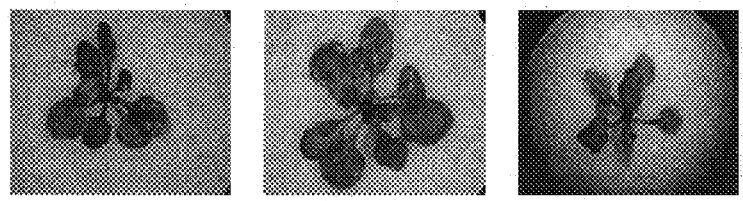
PpCC-2
Drought
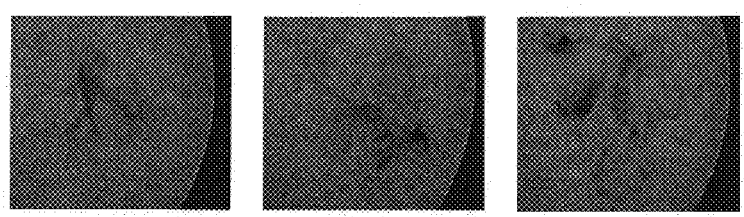
Control
Drought Figure 8
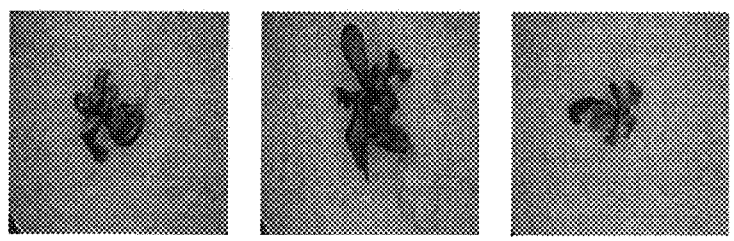
PpCC-3
Drought
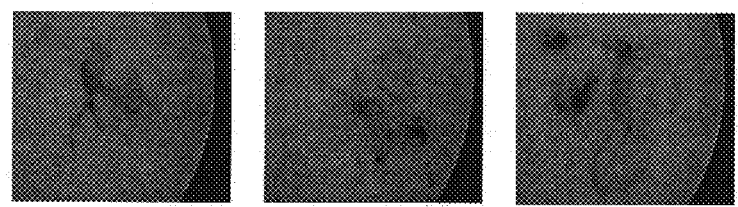
Control
Drought

SEQUENCE LISTING

```
<160> NUMBER OF SEQ ID NOS: 34

<210> SEQ ID NO 1
<211> LENGTH: 887
<212> TYPE: DNA
<213> ORGANISM: Physcomitrella patens
<220> FEATURE:
<221> NAME/KEY: modified_base
<222> LOCATION: (71)
<223> OTHER INFORMATION: a, t, c, g, other or unknown

<400> SEQUENCE: 1
cgggagttgg tgatcttcag catgctcgta gttgacaagg gaggtaggat tgtttgaccc      60
aaggtgtgta nagaagggga tagccatgta cagcaacttc aaagagcagg ccatagaata    120
ttgtgcgtca agccgtagcg gaagacaacg cagggaacta tgccaaagcg tttccgctgt    180
acatgaacgc gcttgagtac ttcaagacgc atctaaagta tgagaagaat cccaaaatca    240
aggaggccat cactcagaag ttcacggagt atttgaggag ggcggaggag attcgagccg    300
ttttggacga tggccccact ggaccctctg caaatggaga cgcggcagtt caagctaaac    360
cgaagtcgaa atcaggaag aaggatggtg gcggggtga tggtgatggt gacagcgagg    420
atcccgacca gcagaagctg agatcagggc tgaactcggc aatcatacgg gaaaagccaa    480
atgttcggtg ggctgatgtt gctggacttg aaagtgccaa gcaggcgttg caggaggcag    540
tgatcttgcc cgtgaagttt ccccaatttt tcacagggaa gcgaagaaca tggcgagcat    600
ttttgtggta tgggcccccc gggactggaa aatcgtatct tgcaaaagct gttgctacgg    660
aagctgattc tacattcttt agtatttcct cttcagactt ggtgtcaaag tggatgggag    720
agagtgagaa gcttgttgca aatctgtttc aaatggcccg tgaagctgct ccatccatca    780
tcttcataga cgagattgat tctttatgcg gtactcgagg tgaaggaaat gagagcgagg    840
cttcacgtcg tatcaagact gagttgctag ttcaaatgca gggtgtc                   887

<210> SEQ ID NO 2
<211> LENGTH: 723
<212> TYPE: DNA
<213> ORGANISM: Physcomitrella patens

<400> SEQUENCE: 2
cggcaccagg gagatcgtat tgaggtaaca ggagttttca aggccatggc agttcgagtt      60
```

```
ggtccgaatc aacgaacatt acgagcattg tataagacct acatcgattg cgtgcacgtc      120
aagaagtctg acaggggtcg actgcaaact gaagatccta tggagatgga taaggagaat      180
gatatgtatg ctgggtatca tgaaagtgat acttcagaag ctgctaatga agcaaagatt      240
caaaaactta agagctgtc caagctcccg gacatttatg atagactttc aaggtcgctg       300
gctccaagca tttgggagct tgaagatatt aaaaaggggtc ttctttgcca gctctttggt     360
gggaaggcta agaaaattcc atctggagca tctttccgag gtgacatcaa tgttttactt      420
gttggggacc tggtaccag taaatctcag ctgcttcagt atgtgcacaa gatagctcct       480
cgtggaatct acactagtgg gcgaggaagt tcggcggttg ggctgacagc gtatgtaaac      540
gaaggatcca gaaactcgag agacggtatt ggagagcgga gctttggttc ttagtgatcg      600
tgggatatgc tgtatcgatg agttcgacaa aatgtctgat aatgcccgaa gcatgcttca      660
tgaggtaatg gagcaacaaa cggtatctgg acccaagcgg ttcatgctcg tgaagccgag      720
ttg                                                                    723

<210> SEQ ID NO 3
<211> LENGTH: 566
<212> TYPE: DNA
<213> ORGANISM: Physcomitrella patens

<400> SEQUENCE: 3
gcaccagccg ctttggaatc ccatccctcg gttgcataga cacaagggga ttcagtgtag       60
tgatacgttg tgcatatttg gtgttgcaag attttttggtt tcttgattgt tagctatggc    120
gtctgcaaca gcggctacaa tggcgtccct cctcacgcct gggtctctcc gacgcggttt      180
gggtagccag gaatcgtcga cccaatttgc tcccctagct ggtcctcgta agacatcagt      240
ttcgcgtagg gtgactgcta gcgctagtgg gaagaacgac aatggagtcg tggaagatgt      300
ggatatgggg aagcggggta tgttgaaagg cgtagcggga gctttggctg cagttctccc      360
tgctgttatc gcgaagaaag cttcagcagc tgaggagcag ggcgtagcgt cttccaggat      420
gtcctactcg aggttttttgg agtatttgga tatggaccgt gtgaagaagt tgacttgtat     480
gaaaatggga ccatagcaat tgtggaggct gtatccctg aattgggcaa cagagtgcaa       540
cgcgtacgcg tgcagctccc cggaac                                          566

<210> SEQ ID NO 4
<211> LENGTH: 1564
<212> TYPE: DNA
<213> ORGANISM: Physcomitrella patens

<400> SEQUENCE: 4
gcgatatcga cccaaggtgt gtagagaagg ggatagccat gtacagcaac ttcaaagagc       60
aggccataga atatgtgcgt caagccgtag cggaagacaa cgcagggaac tatgccaaag      120
cgtttccgct gtacatgaac gcgcttgagt acttcaagac gcatctaaag tatgagaaga     180
atcccaaaat caaggaggcc atcactcaga agttcacgga gtatttgagg agggcggagg      240
agattcgagc cgttttggac gatggccccca ctggaccctc tgcaaatgga gacgcggcag    300
ttcaagctaa accgaagtcg aaatcaggga agaaggatgg tggcgggggt gatggtgatg     360
gtgacagcga ggatcccgag cagcagaagc tgagatcagg gctgaactcg gcaatcatac     420
gggaaaagcc aaatgttcgg tgggctgatg ttgctggact tgaaagtgcc aagcaggcgt     480
tgcaggaggc agtgatcttg cccgtgaagt tccccaatt tttcacaggg aagcgaagac      540
```

-continued

| | |
|---|---|
| catggcgagc attttttgttg tatgggcccc ccgggactgg aaaatcgtat cttgcaaaag | 600 |
| ctgttgctac ggaagctgat tctacattct ttagtatttc ctcttcagac ttggtgtcaa | 660 |
| agtggatggg agagagtgag aagcttgttg caaatctgtt tcaaatggcc cgtgaagctg | 720 |
| ctccatccat catcttcata gacgagattg attctttatg cggtactcga ggtgaaggaa | 780 |
| atgagagcga ggcttcacgt cgtatcaaga ctgagttgct agttcaaatg cagggtgtcg | 840 |
| gcaatcaaga cactaaggtt cttgtgttag ctgctacaaa tacgccctac tcttttggatc | 900 |
| aggcggtgag cgacgtttc gacaagcgta tctacatccc actaccggag tctaaggctc | 960 |
| ggcagcacat gtttaaggtg catttgggag atacgccaaa caacctgact gaacgtgatt | 1020 |
| atgaggatct ggctaggaag actgatgggt tttcaggctc ggatattgca gtttgtgtga | 1080 |
| aagatgtact atttgagcct gttcgtaaga cccaagatgc tatgcatttc aaaagaatta | 1140 |
| ataccaaaga aggagagatg tggatgcctt gtgggccccg agaaccaggt gctaggcaaa | 1200 |
| ccactatgac ggagcttgcc gctgaagggc aggcatcgaa gattttacca cctccaatca | 1260 |
| caaaatcaga tttcgacaaa gtcctcgcaa agcagaggcc cactgtcagc aaaggcgacc | 1320 |
| ttattattca agagaaattc accaaagaat ttggtgaaga aggttgaatg gtgcttcgag | 1380 |
| ttaagaattt ggaaggttct gggttacgga agacagacga aatagaacgt cgtaggtacg | 1440 |
| gtagcctaag agtaaattac ggaagttttc cgacttgcca gttgtgcact cttttcaacat | 1500 |
| gaagggaagg aagctacttg tcggttgcct tttcatgggt gagttgcatc agtcgcgagc | 1560 |
| tcgc | 1564 |

<210> SEQ ID NO 5
<211> LENGTH: 4348
<212> TYPE: DNA
<213> ORGANISM: Physcomitrella patens

<400> SEQUENCE: 5

| | |
|---|---|
| atggcgcgcc gcactcacgt gaggaattgc acctccttgt tctgcgacgg ttccattctt | 60 |
| tttggttttt agtttgcaaa tcttgatcgt ggagttgaga aaaagggcgg ttcgttgtct | 120 |
| tgaggtgttc ttgttgattg ttcgtcatgg aaaataatga tgcacttgac attggagccg | 180 |
| tgtcgtcccc atatccttcg caatctgaag gagtgtctac gccattgccg caagtaacat | 240 |
| caccgagctt cgacaatgca gcctcacccg tggccgggcg gagggccgta cggcagaccc | 300 |
| ctacatctgc agttcgaagg agagggagag aaacggattc cgctcgtcgt aggaggagtc | 360 |
| gatctcgcag tttaggcaat tctgttttata gttcccctta cgatgcgggg actcctggaa | 420 |
| ctcctggaac tccagtggct actccggttt acgctacccc agtcggtaca cctatgggta | 480 |
| ccccatcgtt ccatcgtggc acgccacagt acaaacagcg cagtgagctt ggttcccagg | 540 |
| ggaagcctct acatcggaga cgtcgatctc aatccagaga acccgggcat cgatctcctt | 600 |
| caagggaacc tagtgctgat gggcgtccct ctgaatctgc tgagccagat gacactttgg | 660 |
| gtggagaata tgcttatgtt tggggacgaa atgttaacat tccagatgtg cttagggcga | 720 |
| tcgtcgatt tctccacaat tatcgttcga gtgctcatga tcttaattcc aagtacatcc | 780 |
| agatcataga ggagactgtg gagcgtgagg aggatactct aaatatcgac atgtcagaca | 840 |
| tttatgacca tgatcctgat ctatacgcaa aaattgttcg ataccactc gacatcatcc | 900 |
| ccctgttgga cactgagtgt caggaagttg ctacctcttt actaccaacg tttgagaagc | 960 |
| atattgaggc cagacctttc aatctcaaag catcggtgca catgcgtgaa ctcaaccctt | 1020 |
| cagatataga caaattggtt tctgttaaag gaatggttat ccggtgcagt tctatcatac | 1080 |

```
ctgaaattaa gggggccttc ttcaaatgtt tagtgtgtgg tcactcgcct ccgctagtta    1140
cagttgttaa agggcgggtt gaggagccaa caaggtgtga aaagccagaa tgtgcagcac    1200
ggaatgctat gtctcttatt cacaatcgat gcacttttgc aaataagcag atagtgcgtc    1260
ttcaagaaac tccagatgcc attcctgaag gagagactcc acacacagtc agcatgtgtt    1320
tatacaacac tatggttgat gctgtgaagc ctggagatcg tattgaggta acaggagttt    1380
tcaaggccat ggcagttcga gttggtcatg gcgcgccgca ctcacgtgag gaattgcacc    1440
tccttgttct gcgacggttc cattcttttt ggttttttagt ttgcaaatct tgatcgtgga    1500
gttgagaaaa agggcggttc gttgtcttga ggtgttcttg ttgattgttc gtcatggaaa    1560
ataatgatgc acttgacatt ggagccgtgt cgtccccata tccttcgcaa tctgaaggag    1620
tgtctacgcc attgccgcaa gtaacatcac cgagcttcga caatgcagcc tcacccgtgg    1680
ccgggcggag ggccgtacgg cagacccta catctgcagt tcgaaggaga gggagagaaa     1740
cggattccgc tcgtcgtagg aggagtcgat ctcgcagttt aggcaattct gtttatagtt    1800
ccccttacga tgcggggact cctggaactc ctggaactcc agtggctact ccggtttacg    1860
ctaccccagt cggtacacct atgggtaccc catcgttcca tcgtggcacg ccacagtaca    1920
aacagcgcag tgagcttggt tcccagggga agcctctaca tcgagacgt cgatctcaat     1980 ccagagaacc cggcatcga tctccttcaa gggaacctag tgctgatggg cgtccctctg     2040
aatctgctga ccagatgac actttgggtg gagaatatgc ttatgtttgg gggacgaatg     2100
ttaacattcc agatgtgctt agggcgattc gtcgatttct ccacaattat cgttcgagtg    2160
ctcatgatct taattccaag tacatccaga tcatagagga gactgtggag cgtgaggagg    2220
atactctaaa tatcgacatg tcagacattt atgaccatga tcctgatcta tacgcaaaaa    2280
ttgttcgata cccactcgac atcatccccc tgttggacac tgagtgtcag gaagttgcta    2340
cctctttact accaacgttt gagaagcata ttgaggccag accttttcaat ctcaaagcat    2400 cggtgcacat gcgtgaactc aacccttcag atatagacaa attggtttct gttaaaggaa    2460
tggttatccg gtgcagttct atcatacctg aaattaaggg ggccttcttc aaatgtttag    2520
tgtgtggtca ctcgcctccg ctagttacag ttgttaaagg gcgggttgag gagccaacaa    2580
ggtgtgaaaa gccagaatgt gcagcacgga atgctatgtc tcttattcac aatcgatgca    2640
cttttgcaaa taagcagata gtgcgtcttc aagaaactcc agatgccatt cctgaaggag    2700
agactccaca cacagtcagc atgtgtttat acaacactat ggttgatgct gtgaagcctg    2760
gagatcgtat tgaggtaaca ggagttttca aggccatggc agttcgagtt ggtccgaatc    2820
aacgaacatt acgagcattg tataagacct acatcgattg cgtgcacgtc aagaagtctg    2880 acagggtcg actgcaaact gaagatccta tggagatgga taggagaat gatatgtatg      2940 ctgggtatca tgaaagtgat acttcagaag ctgctaatga agcaaagatt caaaaactta    3000
aagagctgtc caagctcccg ggcatttatg atagactttc aaggtcgctg gctccaagca    3060
tttgggagct tgaagatatt aaaaagggtc ttctttgcca gctctttggt gggaaggcta    3120
agaaaattcc atctggagca tctttccgag gtgacatcaa tgttttactt gttggggacc    3180
ctggtaccag taaatctcag ctgcttcagt atgtgcacaa gatagctcct cgtggaatct    3240
acactagtgg gcgaggaagt tcggcggttg gctgacagc gtatgtaacg aaggatccag      3300
aaactcgaga gacggtattg gagagcggag cttttggttct tagtgatcgt gggatatgct    3360
gtatcgatga gttcgacaaa atgtctgata atgcccgaag catgcttcat gaggtaatgg    3420
```

-continued

| | |
|---|---:|
| agcaacaaac ggtatctgta gccaaagggg gtatcattgc ctcgctgaac gctcggacgt | 3480 |
| ctgtccttgc atgtgcaaat cctagtgggt cccgatacaa tgcgcgcctt tctgtgattg | 3540 |
| ataacatcca gcttcctcca actctacttt ctagatttga tttaatttac ttaatgctcg | 3600 |
| acaaaccaga cgagcaaaac gatcgtcgtc tcgccaggca tctcgtggct ttacactatg | 3660 |
| aaaactatga agtttcaaag caggacgcct tagatctaca aacacttacc gcgtatatca | 3720 |
| cctatgctcg tcagcatgta catcctacat taagtgatga agctgctgaa gatttgatta | 3780 |
| atggctatgt tgagatgcgc caaaagggca actttcctgg aagcagtaaa aaggtgataa | 3840 |
| cagccacacc tcggcaactc gaaagtatga ttcgtatcag tgaagcccta gctcgaatga | 3900 |
| gattttctga agtggtagag aaagttgatg cagcagaagc tgtgcgcctt ttagacgtcg | 3960 |
| ctttgcagca atctgctact gatcatgcaa caggtacgat agacatggat cttatcacga | 4020 |
| ctggagtgtc ggccagcgag cgtattcgtc gggccaactt gctagctgct ctgcgagagc | 4080 |
| ttatagcaga taaaatttca cctggcagct cctctggctt gaagaccagt cagcttcttg | 4140 |
| aggatatccg gagccaaagc agtgtggacg ttagtttgca ggatattaaa aatgctctgg | 4200 |
| gtagcctcca aggagaaggc tttcttactg tccatggtga catagtcaag agagtttgag | 4260 |
| acagtttcta actgttcgaa tccatgagct ataactctga acgaaaggga aaacctccag | 4320 |
| tttcccatgc gcaattccca gagctcgc | 4348 |

<210> SEQ ID NO 6
<211> LENGTH: 2237
<212> TYPE: DNA
<213> ORGANISM: Physcomitrella patens

<400> SEQUENCE: 6

| | |
|---|---:|
| atcccgggtg atacgttgtg catatttggt gttgcaagtt ttttggtttc ttgattgtta | 60 |
| gctatggcgt ctgcaacagc ggctacaatg gcgtccctcc tcacgcctgg gtctctccga | 120 |
| cgcggttggg gtagccagga atcgtcgacc caatttgctc ccctagctgg tcctcgtaag | 180 |
| acatcagttt cgcgtagggt gactgctagc gctagtggga agaacgacaa tggagtcgtg | 240 |
| gaagatgtgg atatggggaa gcggggtatg ttgaaaggcg tagcgggagc tttggctgca | 300 |
| gttctccctg ctgttatcgc gaagaaagct tcagcagctg aggagcaggg cgtagcgtct | 360 |
| tccaggatgt cctactcgag gttttttggag tatttggata tggaccgtgt gaagaaggtt | 420 |
| gacttgtatg aaaatgggac catagcaatt gtggaggctg tatcccctga attgggcaac | 480 |
| agagtacaac gcgtacgcgt gcagctcccc ggaactagct ccgaattgtt gtcgaagttt | 540 |
| agatcgaaga atgtagattt tgccgcacac agcccacaag aggactctgg ctctgtcatt | 600 |
| ttgaacctca tcggaaattt ggctttcccc ttgttgctcg ttggaggtct gttcttcttg | 660 |
| tctcgtagat cccaaggtgg tatgggacct ggcggtcctg ggaacccgat ggccttcggg | 720 |
| aagtccaagg ccaagttcca gatggagccc aacacgggca ttacattcca agatgttgcg | 780 |
| ggagtagacg aggccaagca agacttcatg gaggttgtgg agttcttgaa gcggcctgag | 840 |
| agattcacag cagtgggcgc taaaatccca aagggagtgt tgctggttgg accacccggt | 900 |
| accggaaaga ctctattggc gaaggccatc gctggggaag ctggagtacc attcttctcc | 960 |
| atctctgggt ctgagttcgt ggaaatgttc gtgggagtgg gagcttcccg tgtgagggac | 1020 |
| ttgttcaaga aggcgaaaga gaatgctccc tgcattgtgt ttgtggatga gattgatgcc | 1080 |
| gttggaagac agagaggaac tggaattgga ggaggcaatg atgagcgtga gcagacgttg | 1140 |
| aatcagttgt tgacggagat ggacggtttc gaaggaaaca ctggtgtgat tgtcattgct | 1200 |

-continued

```
gccaccaaca gggctgatat tctcgacgct gccttgcttc gtcctggaag attcgacaga    1260
caggtttccg tggatgttcc ggacgtgaag ggaaggactg acatcctcaa ggtgcatgct    1320
agtaacaaga agttcgccga tgatgtgtct ctggatatca ttgccatgag acaccaggg     1380 ttcagtggag ctgacttggc caacttgttg aacgaagcag ctatcttgac cggaaggaga    1440
ggaaagacag ccatcagtgc taaggagatt gacgattcaa ttgacagaat cgttgccggg    1500
atggaaggta ccgtcatgac ggacggcaag agcaagagtc ttgttgcata ccacgaagtc    1560
ggccatgcta tctgcgggac tttgactccc ggacacgacg ccgtgcaaaa ggtcaccctc    1620
attcctagag gtcaggcccg tggtctcacc tggtttattc ccggagaaga cccgactttg    1680
atttcaaagc agcaaatctt tgcccgtatt gttggtgctc ttggtggtag ggctaccgag    1740
caggttgtct tcggtgatgc tgaagttacg actggagcgt ccagtgattt gcagcaagtt    1800
acttctatgg ccaagcagat ggtcacagta ttcggtatgt cagacatcgg cccatgggct    1860
ttgatggacc cttcatccca gggaggagat atgattatgc gtatgatggc acgtaactcc    1920
atgtccgaga agttggctga ggacatcgac aaggctgtga aggctatctc tgacgaggcc    1980
tacgaagtcg cactgggtca cattaggaac aaccgcacgg ccatggacaa gattgtagag    2040
gttctgcttg agaaggagac tttgtccggc gccgagttta gggctattct ttcggaatac    2100
acagagattc ctgctgaaaa ccgtgtatca gacaaccagg ccgcacctgt agctgtttga    2160
agtgatcaga agcaagggtg tttgtgaaca caatcgtgta ggttttggag catcgacgct    2220
cttgtatcag agctcgc                                                   2237
```

<210> SEQ ID NO 7
<211> LENGTH: 442
<212> TYPE: PRT
<213> ORGANISM: Physcomitrella patens

<400> SEQUENCE: 7

```
Met Tyr Ser Asn Phe Lys Glu Gln Ala Ile Glu Tyr Val Arg Gln Ala
  1               5                  10                  15

Val Ala Glu Asp Asn Ala Gly Asn Tyr Ala Lys Ala Phe Pro Leu Tyr
             20                  25                  30

Met Asn Ala Leu Glu Tyr Phe Lys Thr His Leu Lys Tyr Glu Lys Asn
         35                  40                  45

Pro Lys Ile Lys Glu Ala Ile Thr Gln Lys Phe Thr Glu Tyr Leu Arg
     50                  55                  60

Arg Ala Glu Glu Ile Arg Ala Val Leu Asp Asp Gly Pro Thr Gly Pro
 65                  70                  75                  80

Ser Ala Asn Gly Asp Ala Ala Val Gln Ala Lys Pro Lys Ser Lys Ser
                 85                  90                  95

Gly Lys Lys Asp Gly Gly Gly Asp Gly Asp Gly Asp Ser Glu Asp
            100                 105                 110

Pro Glu Gln Gln Lys Leu Arg Ser Gly Leu Asn Ser Ala Ile Ile Arg
        115                 120                 125

Glu Lys Pro Asn Val Arg Trp Ala Asp Val Ala Gly Leu Glu Ser Ala
    130                 135                 140

Lys Gln Ala Leu Gln Glu Ala Val Ile Leu Pro Val Lys Phe Pro Gln
145                 150                 155                 160

Phe Phe Thr Gly Lys Arg Arg Pro Trp Arg Ala Phe Leu Leu Tyr Gly
                165                 170                 175

Pro Pro Gly Thr Gly Lys Ser Tyr Leu Ala Lys Ala Val Ala Thr Glu
```

```
                180                 185                 190
Ala Asp Ser Thr Phe Phe Ser Ile Ser Ser Ser Asp Leu Val Ser Lys
                195                 200                 205

Trp Met Gly Glu Ser Glu Lys Leu Val Ala Asn Leu Phe Gln Met Ala
            210                 215                 220

Arg Glu Ala Ala Pro Ser Ile Ile Phe Ile Asp Glu Ile Asp Ser Leu
225                 230                 235                 240

Cys Gly Thr Arg Gly Glu Gly Asn Glu Ser Glu Ala Ser Arg Arg Ile
                245                 250                 255

Lys Thr Glu Leu Leu Val Gln Met Gln Gly Val Gly Asn Gln Asp Thr
            260                 265                 270

Lys Val Leu Val Leu Ala Ala Thr Asn Thr Pro Tyr Ser Leu Asp Gln
        275                 280                 285

Ala Val Arg Arg Arg Phe Asp Lys Arg Ile Tyr Ile Pro Leu Pro Glu
        290                 295                 300

Ser Lys Ala Arg Gln His Met Phe Lys Val His Leu Gly Asp Thr Pro
305                 310                 315                 320

Asn Asn Leu Thr Glu Arg Asp Tyr Glu Asp Leu Ala Arg Lys Thr Asp
                325                 330                 335

Gly Phe Ser Gly Ser Asp Ile Ala Val Cys Val Lys Asp Val Leu Phe
            340                 345                 350

Glu Pro Val Arg Lys Thr Gln Asp Ala Met His Phe Lys Arg Ile Asn
        355                 360                 365

Thr Lys Glu Gly Glu Met Trp Met Pro Cys Gly Pro Arg Glu Pro Gly
        370                 375                 380

Ala Arg Gln Thr Thr Met Thr Glu Leu Ala Ala Glu Gly Gln Ala Ser
385                 390                 395                 400

Lys Ile Leu Pro Pro Pro Ile Thr Lys Ser Asp Phe Asp Lys Val Leu
                405                 410                 415

Ala Lys Gln Arg Pro Thr Val Ser Lys Gly Asp Leu Ile Ile Gln Glu
            420                 425                 430

Lys Phe Thr Lys Glu Phe Gly Glu Gly
        435                 440

<210> SEQ ID NO 8
<211> LENGTH: 901
<212> TYPE: PRT
<213> ORGANISM: Physcomitrella patens

<400> SEQUENCE: 8

Met Glu Asn Asn Asp Ala Leu Asp Ile Gly Ala Val Ser Ser Pro Tyr
1               5                   10                  15

Pro Ser Gln Ser Glu Gly Val Ser Thr Pro Leu Pro Gln Val Thr Ser
            20                  25                  30

Pro Ser Phe Asp Asn Ala Ala Ser Pro Val Ala Gly Arg Arg Ala Val
        35                  40                  45

Arg Gln Thr Pro Thr Ser Ala Val Arg Arg Gly Arg Glu Thr Asp
    50                  55                  60

Ser Ala Arg Arg Arg Ser Arg Ser Arg Ser Leu Gly Asn Ser Val
65                  70                  75                  80

Tyr Ser Ser Pro Tyr Asp Ala Gly Thr Pro Gly Thr Pro Gly Thr Pro
                85                  90                  95

Val Ala Thr Pro Val Tyr Ala Pro Val Gly Thr Pro Met Gly Thr
            100                 105                 110
```

```
Pro Ser Phe His Arg Gly Thr Pro Gln Tyr Lys Gln Arg Ser Glu Leu
        115                 120                 125

Gly Ser Gln Gly Lys Pro Leu His Arg Arg Arg Ser Gln Ser Arg
130                 135                 140

Glu Pro Gly His Arg Ser Pro Ser Arg Glu Pro Ser Ala Asp Gly Arg
145                 150                 155                 160

Pro Ser Glu Ser Ala Glu Pro Asp Asp Thr Leu Gly Gly Glu Tyr Ala
                165                 170                 175

Tyr Val Trp Gly Thr Asn Val Asn Ile Pro Asp Val Leu Arg Ala Ile
            180                 185                 190

Arg Arg Phe Leu His Asn Tyr Arg Ser Ser Ala His Asp Leu Asn Ser
        195                 200                 205

Lys Tyr Ile Gln Ile Ile Glu Glu Thr Val Glu Arg Glu Glu Asp Thr
210                 215                 220

Leu Asn Ile Asp Met Ser Asp Ile Tyr Asp His Asp Pro Asp Leu Tyr
225                 230                 235                 240

Ala Lys Ile Val Arg Tyr Pro Leu Asp Ile Ile Pro Leu Leu Asp Thr
                245                 250                 255

Glu Cys Gln Glu Val Ala Thr Ser Leu Leu Pro Thr Phe Glu Lys His
            260                 265                 270

Ile Glu Ala Arg Pro Phe Asn Leu Lys Ala Ser Val His Met Arg Glu
        275                 280                 285

Leu Asn Pro Ser Asp Ile Asp Lys Leu Val Ser Val Lys Gly Met Val
290                 295                 300

Ile Arg Cys Ser Ser Ile Ile Pro Glu Ile Lys Gly Ala Phe Phe Lys
305                 310                 315                 320

Cys Leu Val Cys Gly His Ser Pro Pro Leu Val Thr Val Lys Gly
                325                 330                 335

Arg Val Glu Glu Pro Thr Arg Cys Glu Lys Pro Glu Cys Ala Ala Arg
            340                 345                 350

Asn Ala Met Ser Leu Ile His Asn Arg Cys Thr Phe Ala Asn Lys Gln
        355                 360                 365

Ile Val Arg Leu Gln Glu Thr Pro Asp Ala Ile Pro Glu Gly Glu Thr
370                 375                 380

Pro His Thr Val Ser Met Cys Leu Tyr Asn Thr Met Val Asp Ala Val
385                 390                 395                 400

Lys Pro Gly Asp Arg Ile Glu Val Thr Gly Val Phe Lys Ala Met Ala
                405                 410                 415

Val Arg Val Gly Pro Asn Gln Arg Thr Leu Arg Ala Leu Tyr Lys Thr
            420                 425                 430

Tyr Ile Asp Cys Val His Val Lys Lys Ser Asp Arg Gly Arg Leu Gln
        435                 440                 445

Thr Glu Asp Pro Met Glu Met Asp Lys Glu Asn Asp Met Tyr Ala Gly
450                 455                 460

Tyr His Glu Ser Asp Thr Ser Glu Ala Ala Asn Glu Ala Lys Ile Gln
465                 470                 475                 480

Lys Leu Lys Glu Leu Ser Lys Leu Pro Gly Ile Tyr Asp Arg Leu Ser
                485                 490                 495

Arg Ser Leu Ala Pro Ser Ile Trp Glu Leu Glu Asp Ile Lys Lys Gly
            500                 505                 510

Leu Leu Cys Gln Leu Phe Gly Gly Lys Ala Lys Lys Ile Pro Ser Gly
        515                 520                 525

Ala Ser Phe Arg Gly Asp Ile Asn Val Leu Leu Val Gly Asp Pro Gly
```

-continued

```
                530                 535                 540
Thr Ser Lys Ser Gln Leu Leu Gln Tyr Val His Lys Ile Ala Pro Arg
545                 550                 555                 560
Gly Ile Tyr Thr Ser Gly Arg Gly Ser Ser Ala Val Gly Leu Thr Ala
                565                 570                 575
Tyr Val Thr Lys Asp Pro Glu Thr Arg Glu Thr Val Leu Glu Ser Gly
                580                 585                 590
Ala Leu Val Leu Ser Asp Arg Gly Ile Cys Cys Ile Asp Glu Phe Asp
                595                 600                 605
Lys Met Ser Asp Asn Ala Arg Ser Met Leu His Glu Val Met Glu Gln
                610                 615                 620
Gln Thr Val Ser Val Ala Lys Gly Gly Ile Ile Ala Ser Leu Asn Ala
625                 630                 635                 640
Arg Thr Ser Val Leu Ala Cys Ala Asn Pro Ser Gly Ser Arg Tyr Asn
                645                 650                 655
Ala Arg Leu Ser Val Ile Asp Asn Ile Gln Leu Pro Pro Thr Leu Leu
                660                 665                 670
Ser Arg Phe Asp Leu Ile Tyr Leu Met Leu Asp Lys Pro Asp Glu Gln
                675                 680                 685
Asn Asp Arg Arg Leu Ala Arg His Leu Val Ala Leu His Tyr Glu Asn
                690                 695                 700
Tyr Glu Val Ser Lys Gln Asp Ala Leu Asp Leu Gln Thr Leu Thr Ala
705                 710                 715                 720
Tyr Ile Thr Tyr Ala Arg Gln His Val His Pro Thr Leu Ser Asp Glu
                725                 730                 735
Ala Ala Glu Asp Leu Ile Asn Gly Tyr Val Glu Met Arg Gln Lys Gly
                740                 745                 750
Asn Phe Pro Gly Ser Ser Lys Lys Val Ile Thr Ala Thr Pro Arg Gln
                755                 760                 765
Leu Glu Ser Met Ile Arg Ile Ser Glu Ala Leu Ala Arg Met Arg Phe
                770                 775                 780
Ser Glu Val Val Glu Lys Val Asp Ala Ala Glu Ala Val Arg Leu Leu
785                 790                 795                 800
Asp Val Ala Leu Gln Gln Ser Ala Thr Asp His Ala Thr Gly Thr Ile
                805                 810                 815
Asp Met Asp Leu Ile Thr Thr Gly Val Ser Ala Ser Glu Arg Ile Arg
                820                 825                 830
Arg Ala Asn Leu Leu Ala Ala Leu Arg Glu Leu Ile Ala Asp Lys Ile
                835                 840                 845
Ser Pro Gly Ser Ser Gly Leu Lys Thr Ser Gln Leu Leu Glu Asp
                850                 855                 860
Ile Arg Ser Gln Ser Ser Val Asp Val Ser Leu Gln Asp Ile Lys Asn
865                 870                 875                 880
Ala Leu Gly Ser Leu Gln Gly Glu Gly Phe Leu Thr Val His Gly Asp
                885                 890                 895
Ile Val Lys Arg Val
                900
```

<210> SEQ ID NO 9
<211> LENGTH: 698
<212> TYPE: PRT
<213> ORGANISM: Physcomitrella patens

<400> SEQUENCE: 9

-continued

```
Met Ala Ser Ala Thr Ala Ala Thr Met Ala Ser Leu Leu Thr Pro Gly
  1               5                  10                  15

Ser Leu Arg Arg Gly Leu Gly Ser Gln Glu Ser Ser Thr Gln Phe Ala
             20                  25                  30

Pro Leu Ala Gly Pro Arg Lys Thr Ser Val Ser Arg Val Thr Ala
             35                  40                  45

Ser Ala Ser Gly Lys Asn Asp Asn Gly Val Val Glu Asp Val Asp Met
         50                  55                  60

Gly Lys Arg Gly Met Leu Lys Gly Val Ala Gly Leu Ala Ala Val
 65                  70                  75                  80

Leu Pro Ala Val Ile Ala Lys Lys Ala Ser Ala Glu Glu Gln Gly
                 85                  90                  95

Val Ala Ser Ser Arg Met Ser Tyr Ser Arg Phe Leu Glu Tyr Leu Asp
             100                 105                 110

Met Asp Arg Val Lys Lys Val Asp Leu Tyr Glu Asn Gly Thr Ile Ala
             115                 120                 125

Ile Val Glu Ala Val Ser Pro Glu Leu Gly Asn Arg Val Gln Arg Val
 130                 135                 140

Arg Val Gln Leu Pro Gly Thr Ser Ser Glu Leu Leu Ser Lys Phe Arg
145                 150                 155                 160

Ser Lys Asn Val Asp Phe Ala Ala His Ser Pro Gln Glu Asp Ser Gly
                 165                 170                 175

Ser Val Ile Leu Asn Leu Ile Gly Asn Leu Ala Phe Pro Leu Leu Leu
             180                 185                 190

Val Gly Gly Leu Phe Phe Leu Ser Arg Arg Ser Gln Gly Gly Met Gly
             195                 200                 205

Pro Gly Gly Pro Gly Asn Pro Met Ala Phe Gly Lys Ser Lys Ala Lys
 210                 215                 220

Phe Gln Met Glu Pro Asn Thr Gly Ile Thr Phe Gln Asp Val Ala Gly
225                 230                 235                 240

Val Asp Glu Ala Lys Gln Asp Phe Met Glu Val Val Glu Phe Leu Lys
             245                 250                 255

Arg Pro Glu Arg Phe Thr Ala Val Gly Ala Lys Ile Pro Lys Gly Val
             260                 265                 270

Leu Leu Val Gly Pro Pro Gly Thr Gly Lys Thr Leu Leu Ala Lys Ala
             275                 280                 285

Ile Ala Gly Glu Ala Gly Val Pro Phe Phe Ser Ile Ser Gly Ser Glu
 290                 295                 300

Phe Val Glu Met Phe Val Gly Val Gly Ala Ser Arg Val Arg Asp Leu
305                 310                 315                 320

Phe Lys Lys Ala Lys Glu Asn Ala Pro Cys Ile Val Phe Val Asp Glu
             325                 330                 335

Ile Asp Ala Val Gly Arg Gln Arg Gly Thr Ile Gly Gly Gly Asn
             340                 345                 350

Asp Glu Arg Glu Gln Thr Leu Asn Gln Leu Leu Thr Glu Met Asp Gly
             355                 360                 365

Phe Glu Gly Asn Thr Gly Val Ile Val Ile Ala Ala Thr Asn Arg Ala
             370                 375                 380

Asp Ile Leu Asp Ala Ala Leu Leu Arg Pro Gly Arg Phe Asp Arg Gln
385                 390                 395                 400

Val Ser Val Asp Val Pro Asp Val Lys Gly Arg Thr Asp Ile Leu Lys
             405                 410                 415

Val His Ala Ser Asn Lys Lys Phe Ala Asp Asp Val Ser Leu Asp Ile
```

```
                    420                 425                 430
Ile Ala Met Arg Thr Pro Gly Phe Ser Gly Ala Asp Leu Ala Asn Leu
            435                 440                 445

Leu Asn Glu Ala Ala Ile Leu Thr Gly Arg Arg Gly Lys Thr Ala Ile
    450                 455                 460

Ser Ala Lys Glu Ile Asp Asp Ser Ile Asp Arg Ile Val Ala Gly Met
465                 470                 475                 480

Glu Gly Thr Val Met Thr Asp Gly Lys Ser Lys Ser Leu Val Ala Tyr
                485                 490                 495

His Glu Val Gly His Ala Ile Cys Gly Thr Leu Thr Pro Gly His Asp
            500                 505                 510

Ala Val Gln Lys Val Thr Leu Ile Pro Arg Gly Gln Ala Arg Gly Leu
        515                 520                 525

Thr Trp Phe Ile Pro Gly Glu Asp Pro Thr Leu Ile Ser Lys Gln Gln
    530                 535                 540

Ile Phe Ala Arg Ile Val Gly Ala Leu Gly Gly Arg Ala Thr Glu Gln
545                 550                 555                 560

Val Val Phe Gly Asp Ala Glu Val Thr Thr Gly Ala Ser Ser Asp Leu
                565                 570                 575

Gln Gln Val Thr Ser Met Ala Lys Gln Met Val Thr Val Phe Gly Met
            580                 585                 590

Ser Asp Ile Gly Pro Trp Ala Leu Met Asp Pro Ser Ser Gln Gly Gly
        595                 600                 605

Asp Met Ile Met Arg Met Met Ala Arg Asn Ser Met Ser Glu Lys Leu
    610                 615                 620

Ala Glu Asp Ile Asp Lys Ala Val Lys Ala Ile Ser Asp Glu Ala Tyr
625                 630                 635                 640

Glu Val Ala Leu Gly His Ile Arg Asn Arg Thr Ala Met Asp Lys
                645                 650                 655

Ile Val Glu Val Leu Leu Glu Lys Glu Thr Leu Ser Gly Ala Glu Phe
            660                 665                 670

Arg Ala Ile Leu Ser Glu Tyr Thr Glu Ile Pro Ala Glu Asn Arg Val
        675                 680                 685

Ser Asp Asn Gln Ala Ala Pro Val Ala Val
    690                 695

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 10
caggaaacag ctatgacc                                                  18

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
ctaaagggaa caaaagctg                                                 19

<210> SEQ ID NO 12
```

```
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 12
tgtaaaacga cggccagt                                                   18

<210> SEQ ID NO 13
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 13
gcgatatcga cccaaggtgt gtagagaagg ggat                                 34

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 14
gcgagctcgc gactgatgca actcacccat gaa                                  33

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 15
cccaaatgct tggagccagc gacct                                           25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 16
gacgtgcacg caatcgatgt aggtc                                           25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 17
agtcgacccc tgtcagactt cttga                                           25

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 18
```

```
atggcgcgcc gcactcacgt gaggaattgc acctcc                              36
```

\<210\> SEQ ID NO 19
\<211\> LENGTH: 32
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 19

```
gcgagctctg ggaattgcgc atgggaaact gg                                  32
```

\<210\> SEQ ID NO 20
\<211\> LENGTH: 25
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 20

```
ctggctaccc aaaccgcgtc ggaga                                          25
```

\<210\> SEQ ID NO 21
\<211\> LENGTH: 35
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 21

```
atcccgggtg atacgttgtg catatttggt gttgc                               35
```

\<210\> SEQ ID NO 22
\<211\> LENGTH: 32
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 22

```
gcgagctctg atacaagagc gtcgatgctc ca                                  32
```

\<210\> SEQ ID NO 23
\<211\> LENGTH: 30
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 23

```
gcgctgcaga tttcatttgg agaggacacg                                     30
```

\<210\> SEQ ID NO 24
\<211\> LENGTH: 35
\<212\> TYPE: DNA
\<213\> ORGANISM: Artificial Sequence
\<220\> FEATURE:
\<223\> OTHER INFORMATION: Description of Artificial Sequence: Primer

\<400\> SEQUENCE: 24

```
cgcggccggc ctcagaagaa ctcgtcaaga aggcg                               35
```

\<210\> SEQ ID NO 25
\<211\> LENGTH: 25
\<212\> TYPE: DNA

```
<213> ORGANISM: Artificial Sequence
<220> FEATURE:
<223> OTHER INFORMATION: Description of Artificial Sequence: Primer

<400> SEQUENCE: 25
gctgacacgc caagcctcgc tagtc                                          25

<210> SEQ ID NO 26
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 26
gcgagctcgc gactgatgca actcacccat gaa                                 33

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 27
gcgagctctg ggaattgcgc atgggaaact gg                                  32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 28
gcgagctctg atacaagagc gtcgatgctc ca                                  32

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 29
gatggtgatg gtgacagcga ggatc                                          25

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 30
cgacgtgaag cctcgctctc atttcc                                         26

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 31
cgatctcctt caagggaacc tagtgctg                                       28
```

```
<210> SEQ ID NO 32
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 32
gagttcacgc atgtgcaccg atgct                                           25

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 33
cgtagcgtct tccaggatgt cctac                                           25

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 34
gcttggcctc gtctactccc gcaac                                           25
```

CELL CYCLE STRESS-RELATED PROTEINS AND METHODS OF USE IN PLANTS

CROSS REFERENCE TO RELATED APPLICATIONS

This application claims the priority benefit of U.S. Provisional Application Ser. No. 60/196,001 filed Apr. 7, 2000.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerance plants using biotechnological methods.

Therefore, what is needed is the identification of the genes and proteins involved in these multi-component processes leading to stress tolerance. Elucidating the function of genes expressed in stress tolerant plants will not only advance our understanding of plant adaptation and tolerance to environmental stresses, but also may provide important information for designing new strategies for crop improvement.

One group of proteins that seems to be associated with stress responses in plants and animals are proteins related to cell division and the cell cycle. Evidence of this relationship is found in the fact that different environmental stresses related to soil water content, incident light and varying leaf temperature all result in a change in the cell division rate. For example, in sunflower leaves, there is a lengthening of the cell cycle associated with stress and aging. Cells in the sunflower leaves tend to arrest at the G1 phase of cell cycle, with no change in the duration of the S-G2-M phases of the cell cycle. Similar observations have been made in other plant species placed under environmental stresses such as sucrose starvation (Van't Hof 1973 Bookhaven Symp. 25:152), oxidative stress (Reichheld et al. 1999 Plant J. 17:647), and water depletion (Schuppler et al. 1998 Plant Physiol. 117:667). These observations and results suggest that there is an important "checkpoint" in the regulation of the cell cycle at the G1-S transition, while other studies suggest another "checkpoint" at the G2-M transition with an arrest of the cells at the G2 phase. It has also been determined that temperature affects the duration of all cell cycle phases by a similar proportion without the preferential arrest in any particular phase of the cell cycle (Tardieu and Granier, 2000 Plant Mol. Biol. 43:555). Although these aforementioned responses to environmental stresses differ, each of these results demonstrates the interconnectivity of the stress response system of these plants and the cell division proteins therein.

The prior art describes several proteins associated with cell division and the cell cycle. One such protein, or protein complex, is the cyclin-CDK complex, which controls progression of the cell cycle phases. Cyclin-dependent protein kinases (CDKs) require cyclin binding for activity and are now widely recognized players at the checkpoints of the eukaryotic cell cycle. The widespread importance of CDKs was realized nearly ten years ago from independent genetic approaches in yeast and biochemical studies of mitotic controls in fertilized eggs of marine invertebrates.

One known component of a CDK complex is a Cdc2 protein termed $P34^{cdc2}$, which is required at both control points (G1-S and G2-M). Several other Cdc2 homologs have been isolated from human and plant species including yeast. One such yeast homolog is Cdc48, which plays a role in the spindle pole body separation in *Saccharomyces cerevisiae*. Another Cdc2 homolog has been described in Arabidopsis (Feiler et al. 1995 EMBO J 14:5626) that is highly expressed in the proliferating cells of the vegetative shoot, root, floral inflorescence and flowers and in rapidly growing cells. The Arabidopsis Cdc48 gene is up regulated in the developing microspores and ovules and down regulated in most differentiated cell types. In addition, this gene has been localized to the nucleus and during cytokinesis to the fragmoplast.

Another group of proteins involved in cell division and the cell cycle are pRB proteins. Growing evidence suggests that pRB-like proteins in plants might be among the nuclear targets of plant CDKs. In mammals, the pRB is central to the regulation of the G1-to-S transition. Phosphorylation of mammalian pRB by cyclin D- and cyclin E-dependent kinases renders the pRB inactive and thereby represses the S phase and promotes DNA replication. Significantly, the pRB-binding motif LXCXE (where X denotes any amino acid) is found in all known plant D cyclins. In plants, LXCXE-dependent interactions between D cyclins from Arabidopsis and maize pRB proteins have been demonstrated in vitro and in a yeast two-hybrid assay. The role of pRBs in plant cell division related signaling cascades is further supported by the fact that several pRBs, and in particular, the maize pRB, contain multiple putative CDK phosphorylation sites and are efficiently phosphorylated in vitro by mammalian G1- and S-specific CDKs. Maize pRB proteins are also known to undergo changes in phosphorylation during the transition to endoreduplication in the endosperm. However, phosphorylation by plant CDKs remains to be demonstrated.

Therefore, although several plant cell cycle proteins have been elucidated, the prior art has yet to describe the plant cell cycle signal transduction cascades in detail. The prior art also fails to describe the relation between plant cell cycle proteins and a plant's response to environmental stress such that a stress tolerant plant can be generated. Accordingly, there is a need to identify genes expressed in stress tolerant plants that have the capacity to confer stress resistance to its host plant and to other plant species. Newly generated stress tolerant plants will have many advantages, such as increasing the range that crop plants can be cultivated by, for example, decreasing the water requirements of a plant species.

SUMMARY OF THE INVENTION

This invention fulfills in part the need to identify new, unique cell cycle proteins capable of conferring stress tolerance to plants upon over-expression. The present invention provides a transgenic plant cell transformed by a Cell Cycle Stress-Related Protein (CCSRP) coding nucleic acid, wherein expression of the nucleic acid sequence in the plant cell results in increased tolerance to environmental stress as compared to a wild type variety of the plant cell. Namely, described herein are the cell cycle proteins 1) Cell Cycle-1 (CC-1); 2) Cell Cycle-2 (CC-2) and 3) Cell Cycle-3 (CC-3), all from *Physcomitrella patens*.

The invention provides in some embodiments that the CCSRP and coding nucleic acid are that found in members of the genus Physcomitrella. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a CCSRP coding nucleic acid, wherein the plant is true breeding for increased tolerance to environmental stress as compared to a wild type variety of the plant. The invention further provides a seed produced by a transgenic plant expressing a CCSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated CCSRP as described below. The invention further provides an isolated CCSRP coding nucleic acid, wherein the CCSRP coding nucleic acid codes for a CCSRP as described below.

The invention further provides an isolated recombinant expression vector comprising a CCSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a CCSRP coding nucleic acid, wherein expression of the nucleic acid in the plant results in increased tolerance to environmental stress as compared to a wild type variety of the plant comprising: (a) transforming a plant cell with an expression vector comprising a CCSRP coding nucleic acid, and (b) generating from the plant cell a transgenic plant with an increased tolerance to environmental stress as compared to a wild type variety of the plant. In preferred embodiments, the CCSRP and CCSRP coding nucleic acid are as described below.

The present invention further provides a method of identifying a novel CCSRP, comprising (a) raising a specific antibody response to a CCSRP, or fragment thereof, as described below; (b) screening putative CCSRP material with the antibody, wherein specific binding of the antibody to the material indicates the presence of a potentially novel CCSRP; and (c) identifying from the bound material a novel CCSRP in comparison to known CCSRP. Alternatively, hybridization with nucleic acid probes as described below can be used to identify novel CCSRP nucleic acids.

The present invention also provides methods of modifying stress tolerance of a plant comprising, modifying the expression of a CCSRP in the plant, wherein the CCSRP is as described below. The invention provides that this method can be performed such that the stress tolerance is either increased or decreased. Preferably, stress tolerance is increased in a plant via increasing expression of a CCSRP.

BRIEF DESCRIPTION OF THE DRAWINGS

FIGS. 1(A–C) show the partial cDNA sequences of CC-1 (SEQ ID NO:1), CC-2 (SEQ ID NO:2) and CC-3 (SEQ ID NO:3) from *Physcomitrella patens*.

FIGS. 2(A–C) show the full-length cDNA sequences of CC-1 (SEQ ID NO:4), CC-2 (SEQ ID NO:5) and CC-3 (SEQ ID NO:6) from *Physcomitrella patens*.

FIGS. 3(A–C) show the deduced amino acid sequences of CC-1 (SEQ ID NO:7), CC-2 (SEQ ID NO:8) and CC-3 (SEQ ID NO:9) from *Physcomitrella patens*.

FIG. 5 shows the results of a drought stress test with over-expressing PpCC-1 transgenic plants and wild-type Arabidopsis lines. The transgenic lines display a tolerant phenotype. Individual transformant lines are shown.

FIG. 6 shows the results of a freezing stress test with over-expressing PpCC-1 transgenic plants and wild-type Arabidopsis lines. The transgenic lines display a tolerant phenotype. Individual transformant lines are shown.

FIG. 7 shows the results of a drought stress test with over-expressing PpCC-2 transgenic plants and wild-type Arabidopsis lines. The transgenic lines display a tolerant phenotype. Individual transformant lines are shown.

FIG. 8 shows the results of a drought stress test with over-expressing PpCC-3 transgenic plants and wild-type Arabidopsis lines. The transgenic lines display a tolerant phenotype. Individual transformant lines are shown.

DETAILED DESCRIPTION OF THE INVENTION

Figure 4:
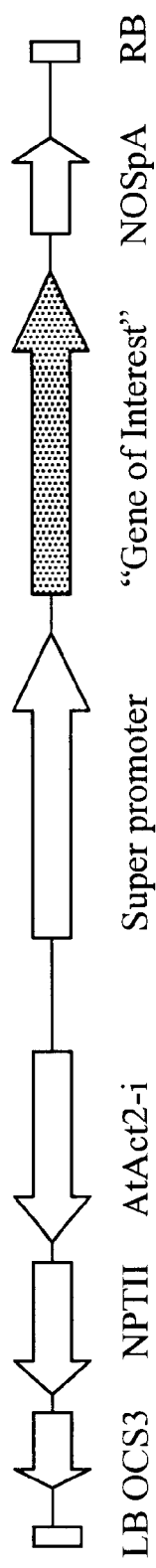
FIG. 4 shows a diagram of the plant expression vector ppBPSsc022 containing the super promoter driving the expression of SEQ ID NOs: 4, 5 and 6 ("Desired Gene"). The components are: NPTII kanamycin resistance gene, AtAct2-i promoter, OCS3 terminator, NOSpA terminator (Jefferson et al., 1987 EMBO J 6:3901–7).

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "Cell Cycle Stress-Related Proteins" (CCSRPs), in no way limits the functionality of those sequences.

The present invention provides a transgenic plant cell transformed by a CCSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a CCSRP coding nucleic acid, wherein the seed contains the CCSRP coding nucleic acid, and wherein the plant is true breeding for increased tolerance to environmental stress as compared to a wild type variety of the plant. The invention further provides a seed produced by a transgenic plant expressing a CCSRP, wherein the seed contains the CCSRP, and wherein the plant is true breeding for increased tolerance to environmental stress as compared to a wild type variety of the plant. The invention also provides an agricultural product produced by any of the below-described transgenic plants, plant parts and plant seeds.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* CCSRPs, CC-1, CC-2 and CC-3, are useful for increasing a plant's tolerance to environmental stress. Accordingly, the present invention provides isolated CCSRPs selected from the group consisting of CC-1, CC-2 and CC-3, and homologs thereof. In preferred embodiments, the CCSRP is selected from 1) a Cell Cycle-1 (CC-1) protein as defined in SEQ ID NO:7; 2) a Cell Cycle-2 (CC-2) protein as defined in SEQ ID NO:8; and 3) a Cell Cycle-3 (CC-3) protein as defined in SEQ ID NO:9 and homologs and orthologs thereof. Homologs and orthologs of the amino acid sequences are defined below.

The CCSRPs of the present invention are preferably produced by recombinant DNA techniques. For example, a nucleic acid molecule encoding the protein is cloned into an expression vector (as described below), the expression vector is introduced into a host cell (as described below) and the CCSRP is expressed in the host cell. The CCSRP can then be isolated from the cells by an appropriate purification scheme using standard protein purification techniques. Alternative to recombinant expression, a CCSRP polypeptide, or peptide can be synthesized chemically using standard peptide synthesis techniques. Moreover, native CCSRP can be isolated from cells (e.g., *Physcomitrella patens*), for example using an anti-CCSRP antibody, which can be produced by standard techniques utilizing a CCSRP or fragment thereof.

The invention further provides an isolated CCSRP coding nucleic acid. The present invention includes CCSRP coding nucleic acids that encode CCSRPs as described herein. In preferred embodiments, the CCSRP coding nucleic acid is selected from 1) a Cell Cycle-1 (CC-1) nucleic acid as defined in SEQ ID NO:4; 2) a Cell Cycle-2 (CC-2) nucleic acid as defined in SEQ ID NO:5; and 3) a Cell Cycle-3 (CC-3) nucleic acid as defined in SEQ ID NO:6 and homologs and orthologs thereof. Homologs and orthologs of the nucleotide sequences are defined below. In one preferred embodiment, the nucleic acid and protein are isolated from the plant genus Physcomitrella. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated CCSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:4, SEQ ID NO:5, SEQ ID NO:6, or a portion thereof, can be isolated using standard molecular biology techniques and the sequence information provided herein. For example, a *P. patens* CCSRP cDNA can be isolated from a *P. patens* library using all or portion of one of the sequences of SEQ ID NO: 1, SEQ ID NO:2 and SEQ ID NO:3. Moreover, a nucleic acid molecule encompassing all or a portion of one of the sequences of SEQ ID NO:1, SEQ ID NO:2 and SEQ ID NO:3 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294–5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2 and SEQ ID NO:3. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to a CCSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:4, SEQ ID NO:5 and SEQ ID NO:6. These cDNAs comprise sequences encoding the CCSRPs (i.e., the "coding region", indicated in Table 1), as well as 5' untranslated sequences and 3' untranslated sequences. It is to be understood that SEQ ID NO:4, SEQ ID NO:5 and SEQ ID NO:6 comprise both coding regions and 5' and 3' untranslated regions. Alternatively, the nucleic acid molecules of the present invention can comprise only the coding region of any of the sequences in SEQ ID NO:4, SEQ ID NO:5 or SEQ ID NO:6 or can contain whole genomic fragments isolated from genomic DNA. A coding region of these sequences is indicated as an "ORF position". The present invention also includes CCSRP coding nucleic acids that encode CCSRPs as described herein. Preferred is a CCSRP coding nucleic acid that encodes a CCSRP selected from the group consisting of, CC-1 (SEQ ID NO:7), CC-2 (SEQ ID NO:8) and CC-3 (SEQ ID NO:9).

Moreover, the nucleic acid molecule of the invention can comprise only a portion of the coding region of one of the sequences in SEQ ID NO:4, SEQ ID NO:5 and SEQ ID NO:6, for example, a fragment which can be used as a probe or primer or a fragment encoding a biologically active portion of a CCSRP. The nucleotide sequences determined from the cloning of the CCSRP genes from *P. patens* allow for the generation of probes and primers designed for use in identifying and/or cloning CCSRP homologs in other cell types and organisms, as well as CCSRP homologs from other mosses and related species.

Portions of proteins encoded by the CCSRP nucleic acid molecules of the invention are preferably biologically active portions of one of the CCSRPs described herein. As used herein, the term "biologically active portion of" a CCSRP is intended to include a portion, e.g., a domain/motif, of a CCSRP that participates in a stress tolerance response in a plant, has an activity as set forth in Table 1, or participates in the transcription of a protein involved in a stress tolerance response in a plant. To determine whether a CCSRP, or a biologically active portion thereof, can participate in transcription of a protein involved in a stress tolerance response in a plant, a stress analysis of a plant comprising the CCSRP may be performed. Such analysis methods are well known to those skilled in the art, as detailed in Example 7. More specifically, nucleic acid fragments encoding biologically active portions of a CCSRP can be prepared by isolating a portion of one of the sequences in SEQ ID NO:7, SEQ ID NO:8 and SEQ ID NO:9, expressing the encoded portion of the CCSRP or peptide (e.g., by recombinant expression in vitro) and assessing the activity of the encoded portion of the CCSRP or peptide.

Biologically active portions of a CCSRP are encompassed by the present invention and include peptides comprising amino acid sequences derived from the amino acid sequence of a CCSRP, e.g., an amino acid sequence of SEQ ID NO:7, SEQ ID NO:8 and SEQ ID NO:9, or the amino acid sequence of a protein homologous to a CCSRP, which include fewer amino acids than a fall length CCSRP or the full length protein which is homologous to a CCSRP, and exhibit at least one activity of a CCSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a CCSRP. Moreover, other biologically active portions in which other regions of the protein are deleted, can be prepared by recombinant techniques and evaluated for one or more of the activities described herein. Preferably, the biologically active portions of a CCSRP include one or more selected domains/motifs or portions thereof having biological activity.

The invention also provides CCSRP chimeric or fusion proteins. As used herein, a CCSRP "chimeric protein" or "fusion protein" comprises a CCSRP polypeptide operatively linked to a non-CCSRP polypeptide. A CCSRP polypeptide refers to a polypeptide having an amino acid sequence corresponding to a CCSRP, whereas a non-CCSRP polypeptide refers to a polypeptide having an amino acid sequence corresponding to a protein which is not substantially homologous to the CCSRP, e.g., a protein that is different from the CCSRP and is derived from the same or a different organism. Within the fusion protein, the term "operatively linked" is intended to indicate that the CCSRP polypeptide and the non-CCSRP polypeptide are fused to each other so that both sequences fulfill the proposed function attributed to the sequence used. The non-CCSRP polypeptide can be fused to the N-terminus or C-terminus of the CCSRP polypeptide. For example, in one embodiment, the fusion protein is a GST-CCSRP fusion protein in which the CCSRP sequences are fused to the C-terminus of the GST sequences. Such fusion proteins can facilitate the purification of recombinant CCSRPs. In another embodiment, the fusion protein is a CCSRP containing a heterologous signal sequence at its N-terminus. In certain host cells (e.g., mammalian host cells), expression and/or secretion of a CCSRP can be increased through use of a heterologous signal sequence.

Preferably, a CCSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A CCSRP encoding nucleic acid can be cloned into such an expression vector such that the fusion moiety is linked in-frame to the CCSRP.

In addition to fragments and fusion proteins of the CCSRPs described herein, the present invention includes homologs and analogs of naturally occurring CCSRPs and CCSRP encoding nucleic acids in a plant. "Homologs" are defined herein as two nucleic acids or proteins that have similar, or "homologous", nucleotide or amino acid sequences, respectively. Homologs include allelic variants, orthologs, paralogs, agonists and antagonists of CCSRPs as defined hereafter. The term "homolog" further encompasses nucleic acid molecules that differ from one of the nucleotide sequences shown in SEQ ID NO:4, SEQ ID NO:5 and SEQ ID NO:6 (and portions thereof) due to degeneracy of the genetic code and thus encode the same CCSRP as that encoded by the nucleotide sequences shown in SEQ ID NO:4, SEQ ID NO:5 or SEQ ID NO:6. As used herein a "naturally occurring" CCSRP refers to a CCSRP amino acid sequence that occurs in nature. Preferably, a naturally occurring CCSRP comprises an amino acid sequence selected from the group consisting of SEQ ID NO:7, SEQ ID NO:8 and SEQ ID NO:9.

An agonist of the CCSRP can retain substantially the same, or a subset, of the biological activities of the CCSRP. An antagonist of the CCSRP can inhibit one or more of the activities of the naturally occurring form of the CCSRP. For example, the CCSRP antagonist can competitively bind to a downstream or upstream member of the cell membrane component metabolic cascade that includes the CCSRP, or bind to a CCSRP that mediates transport of compounds across such membranes, thereby preventing translocation from taking place.

Nucleic acid molecules corresponding to natural allelic variants and analogs, orthologs and paralogs of a CCSRP cDNA can be isolated based on their identity to the *Physcomitrella patens* CCSRP nucleic acids described herein using CCSRP cDNAs, or a portion thereof, as a hybridization probe according to standard hybridization techniques under stringent hybridization conditions. In an alternative embodiment, homologs of the CCSRP can be identified by screening combinatorial libraries of mutants, e.g., truncation mutants, of the CCSRP for CCSRP agonist or antagonist activity. In one embodiment, a variegated library of CCSRP variants is generated by combinatorial mutagenesis at the nucleic acid level and is encoded by a variegated gene library. A variegated library of CCSRP variants can be produced by, for example, enzymatically ligating a mixture of synthetic oligonucleotides into gene sequences such that a degenerate set of potential CCSRP sequences is expressible as individual polypeptides, or alternatively, as a set of larger fusion proteins (e.g., for phage display) containing the set of CCSRP sequences therein. There are a variety of methods that can be used to produce libraries of potential CCSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential CCSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the CCSRP coding regions can be used to generate a variegated population of CCSRP fragments for screening and subsequent selection of homologs of a CCSRP. In one embodiment, a library of coding sequence fragments can be generated by treating a double stranded PCR fragment of a CCSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the CCSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of CCSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify CCSRP homologs (Arkin and Yourvan, 1992 PNAS 89:7811–7815; Delgrave et al., 1993 Protein Engineering 6(3):327–331). In another embodiment, cell based assays can be exploited to analyze a variegated CCSRP library, using methods well known in the art. The present invention further provides a method of identifying a novel CCSRP, comprising (a) raising a specific antibody response to a CCSRP, or a fragment thereof, as described above; (b) screening putative CCSRP material with the antibody, wherein specific binding of the antibody to the material indicates the presence of a potentially novel CCSRP; and (c) analyzing the bound material in comparison to known CCSRP, to determine its novelty.

To determine the percent homology of two amino acid sequences (e.g., one of the sequences of SEQ ID NO:7, SEQ ID NO:8 and SEQ ID NO:9 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions or nucleotide positions are then compared. When a position in one sequence (e.g., one of the sequences of SEQ ID NO:7, SEQ ID NO:8 and SEQ ID NO:9) is occupied by the same amino acid residue as the corresponding position in the other sequence (e.g., a mutant form of the sequence selected from the polypeptide of SEQ ID NO:7, SEQ ID NO:8 and SEQ ID NO:9), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology =numbers of identical positions/total numbers of positions ×100). Preferably, the amino acid sequences included in the present invention are at least about 50–60%, preferably at least about 60–70%, and more preferably at least about 70–80%, 80–90%, 90–95%, and most preferably at least about 96%, 97%, 98%, 99% or more homologous to an entire amino acid sequence shown in SEQ ID NO:7, SEQ ID NO:8 or SEQ ID NO:9. In yet another embodiment, at least about 50–60%, preferably at least about 60–70%, and more preferably at least about 70–80%, 80–90%, 90–95%, and most preferably at least about 96%, 97%, 98%, 99% or more homologous to an entire amino acid sequence encoded by a nucleic acid sequence shown in SEQ ID NO:4, SEQ ID NO:5 or SEQ ID NO:6. In other embodiments, the preferable length of sequence comparison for proteins is at least 15 amino acid residues, more preferably at least 25 amino acid residues, and most preferably at least 35 amino acid residues.

In another preferred embodiment, an isolated nucleic acid molecule of the invention comprises a nucleotide sequence which is at least about 50–60%, preferably at least about 60–70%, more preferably at least about 70–80%, 80–90%, or 90–95%, and even more preferably at least about 95%, 96%, 97%, 98%, 99% or more homologous to a nucleotide sequence shown in SEQ ID NO:4, SEQ ID NO:5 or SEQ ID NO:6, or a portion thereof. The preferable length of sequence comparison for nucleic acids is at least 75 nucleotides, more preferably at least 100 nucleotides and most preferably the entire coding region of the nucleic acid.

It is also preferable that the homologous nucleic acid molecule of the invention encodes a protein or portion thereof which includes an amino acid sequence which is sufficiently homologous to an amino acid sequence of SEQ ID NO:7, SEQ ID NO:8 or SEQ ID NO:9 such that the protein or portion thereof maintains the same or a similar function as the amino acid sequence to which it is compared. Functions of the CCSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above-described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873–5877). Such an algorithm is incorporated into the NBLAST and XBLAST programs of Altschul, et al. (1990 J. Mol. Biol. 215:403–410).

BLAST nucleic acid searches can be performed with the NBLAST program, score=100, wordlength=12 to obtain nucleic acid sequences homologous to the CCSRP nucleic acid molecules of the invention. Additionally, BLAST protein searches can be performed with the XBLAST program, score=50, wordlength=3 to obtain amino acid sequences homologous to CCSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the CCSRPs of the present invention. To obtain gapped alignments for comparison purposes, Gapped BLAST can be utilized as described in Altschul et al. (1997 Nucleic Acids Res. 25:3389–3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., hybridizes under stringent conditions, to one of the nucleotide sequences shown in SEQ ID NO:4, SEQ ID NO:5 and SEQ ID NO:6, or a portion thereof. More particularly, an isolated nucleic acid molecule of the invention is at least 15 nucleotides in length and hybridizes under stringent conditions to the nucleic acid molecule comprising a nucleotide sequence of SEQ ID NO:4, SEQ ID NO:5 or SEQ ID NO:6. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in Current Protocols in Molecular Biology, 6.3.1–6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2× SSC, 0.1% SDS at 50–65° C. Preferably, an isolated nucleic acid molecule of the invention that hybridizes under stringent conditions to a sequence of SEQ ID NO:4, SEQ ID NO:5 or SEQ ID NO:6 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* CCSRP.

Using the above-described methods, and others known to those of skill in the art, one of ordinary skill in the art can isolate homologs of the CCSRPs comprising amino acid sequences shown in SEQ ID NO:7, SEQ ID NO:8 or SEQ ID NO:9. One subset of these homologs is allelic variants. As used herein, the term "allelic variant" refers to a nucleotide sequence containing polymorphisms that lead to changes in the amino acid sequences of a CCSRP and that exist within a natural population (e.g., a plant species or variety). Such natural allelic variations can typically result in 1–5% variance in a CCSRP nucleic acid. Allelic variants can be identified by sequencing the nucleic acid sequence of interest in a number of different plants, which can be readily carried out by using hybridization probes to identify the same CCSRP genetic locus in those plants. Any and all such nucleic acid variations and resulting amino acid polymorphisms or variations in a CCSRP that are the result of natural allelic variation and that do not alter the functional activity of a CCSRP, are intended to be within the scope of the invention.

Moreover, nucleic acid molecules encoding CCSRPs from the same or other species such as CCSRP analogs, orthologs and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631–637). Analogs, orthologs and paralogs of a naturally occurring CCSRP can differ from the naturally occurring CCSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80–85%, more preferably 90%, and most preferably 95%, 96%, 97%, 98% or even 99% identity or homology with all or part of a naturally occurring CCSRP amino acid sequence and will exhibit a function similar to a CCSRP. Orthologs of the present invention are also preferably capable of participating in the stress response in plants. In one embodiment, the CCSRP orthologs maintain the ability to participate in the metabolism of compounds necessary for the construction of cellular membranes in *Physcomitrella patens*, or in the transport of molecules across these membranes.

In addition to naturally-occurring variants of a CCSRP sequence that may exist in the population, the skilled artisan will further appreciate that changes can be introduced by mutation into a nucleotide sequence of SEQ ID NO:4, SEQ ID NO:5 or SEQ ID NO:6, thereby leading to changes in the amino acid sequence of the encoded CCSRP, without altering the functional ability of the CCSRP. For example, nucleotide substitutions leading to amino acid substitutions at "non-essential" amino acid residues can be made in a sequence of SEQ ID NO:4, SEQ ID NO:5 or SEQ ID NO:6. A "non-essential" amino acid residue is a residue that can be altered from the wild-type sequence of one of the CCSRPs without altering the activity of said CCSRP, whereas an "essential" amino acid residue is required for CCSRP activity. Other amino acid residues, however, (e.g., those that are not conserved or only semi-conserved in the domain having CCSRP activity) may not be essential for activity and thus are likely to be amenable to alteration without altering CCSRP activity.

Accordingly, another aspect of the invention pertains to nucleic acid molecules encoding CCSRPs that contain changes in amino acid residues that are not essential for CCSRP activity. Such CCSRPs differ in amino acid sequence from a sequence contained in SEQ ID NO:7, SEQ ID NO:8 or SEQ ID NO:9, yet retain at least one of the CCSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:7, SEQ ID NO:8 or SEQ ID NO:9. Preferably, the protein encoded by the nucleic acid molecule is at least about 50–60% homologous to one of the sequences of SEQ ID NO:7, SEQ ID NO:8 and SEQ ID NO:9, more preferably at least about 60–70% homologous to one of the sequences of SEQ ID NO:7, SEQ ID NO:8 and SEQ ID NO:9, even more preferably at least about 70–80%, 80–90%, 90–95% homologous to one of the sequences of SEQ ID NO:7, SEQ ID NO:8 and SEQ ID NO:9, and most preferably at least about 96%, 97%, 98%, or 99% homologous to one of the sequences of SEQ ID NO:7, SEQ ID NO:8 and SEQ ID NO:9. The preferred CCSRP homologs of the present invention are preferably capable of participating in the a stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a CCSRP homologous to a protein sequence of SEQ ID NO:7, SEQ ID NO:8 or SEQ ID NO:9 can be created by introducing one or more nucleotide substitutions, additions or deletions into a nucleotide sequence of SEQ ID NO:4, SEQ ID NO:5 or SEQ ID NO:6 such that one or more amino acid substitutions, additions or deletions are introduced into the encoded protein. Mutations can be introduced into one of the sequences of SEQ ID NO:4, SEQ ID NO:5 and SEQ ID NO:6 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a CCSRP is preferably replaced with another amino acid residue from the same side chain family. Alternatively, in another embodiment, mutations can be introduced randomly along all or part of a CCSRP coding sequence, such as by saturation mutagenesis, and the resultant mutants can be screened for a CCSRP activity described herein to identify mutants that retain CCSRP activity. Following mutagenesis of one of the sequences of SEQ ID NO:4, SEQ ID NO:5 and SEQ ID NO:6, the encoded protein can be expressed recombinantly and the activity of the protein can be determined by analyzing the stress tolerance of a plant expressing the protein as described in Example 7.

In addition to the nucleic acid molecules encoding the CCSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire CCSRP coding strand, or to only a portion thereof. In one embodiment, an antisense nucleic acid molecule is antisense to a "coding region" of the coding strand of a nucleotide sequence encoding a CCSRP. The term "coding region" refers to the region of the nucleotide sequence comprising codons that are translated into amino acid residues (e.g., the entire coding region of, . . . , comprises nucleotides 1 to . . . ). In another embodiment, the antisense nucleic acid molecule is antisense to a "noncoding region" of the coding strand of a nucleotide sequence encoding a CCSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:4, SEQ ID NO:5 and SEQ ID NO:6, or a portion thereof. A nucleic acid molecule that is complementary to one of the nucleotide sequences shown in SEQ ID NO:4, SEQ ID NO:5 and SEQ ID NO:6 is one which is sufficiently complementary to one of the nucleotide sequences shown in SEQ ID NO:4, SEQ ID NO:5 and SEQ ID NO:6 such that it can hybridize to one of the nucleotide sequences shown in SEQ ID NO:4, SEQ ID NO:5 and SEQ ID NO:6, thereby forming a stable duplex.

Given the coding strand sequences encoding the CCSRPs disclosed herein (e.g., the sequences set forth in SEQ ID NO:4, SEQ ID NO:5 and SEQ ID NO:6), antisense nucleic acids of the invention can be designed according to the rules of Watson and Crick base pairing. The antisense nucleic acid molecule can be complementary to the entire coding region of CCSRP mRNA, but more preferably is an oligonucleotide which is antisense to only a portion of the coding or noncoding region of CCSRP mRNA. For example, the antisense oligonucleotide can be complementary to the region surrounding the translation start site of CCSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a CCSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625–6641). The antisense nucleic acid molecule can also comprise a 2'-o-methylribonucleotide (Inoue et al., 1987 Nucleic Acids Res. 15:6131–6148) or a chimeric RNA-DNA analogue (Inoue et al., 1987 FEBS Lett. 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585–591) can be used to catalytically cleave CCSRP mRNA transcripts to thereby inhibit translation of CCSRP mRNA. A ribozyme having specificity for a CCSRP-encoding nucleic acid can be designed based upon the nucleotide sequence of a CCSRP cDNA, as disclosed herein (i.e., SEQ ID NO:4, SEQ ID NO:5 or SEQ ID NO:6) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in a CCSRP-encoding mRNA. See, e.g., Cech et al. U.S. Pat. No. 4,987,071 and Cech et al. U.S. Pat. No. 5,116,742. Alternatively, CCSRP mRNA can be used to select a catalytic RNA having a specific ribonuclease activity from a pool of RNA molecules. See, e.g., Bartel, D. and Szostak, J. W., 1993 Science 261:1411–1418.

Alternatively, CCSRP gene expression can be inhibited by targeting nucleotide sequences complementary to the regulatory region of a CCSRP nucleotide sequence (e.g., a CCSRP promoter and/or enhancer) to form triple helical structures that prevent transcription of a CCSRP gene in target cells. See generally, Helene, C., 1991 Anticancer Drug Des. 6(6):569–84; Helene, C. et al., 1992 Ann. N.Y. Acad. Sci. 660:27–36; and Maher, L. J., 1992 Bioassays 14(12): 807–15.

In addition to the CCSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. A typical group of nucleic acids attached to a moiety are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:4, SEQ ID NO:5 and SEQ ID NO:6, an anti-sense sequence of one of the sequences set forth in SEQ ID NO:4, SEQ ID NO:5 and SEQ ID NO:6, or naturally occurring mutants thereof. Primers based on a nucleotide sequence of SEQ ID NO:4, SEQ ID NO:5 or SEQ ID NO:6 can be used in PCR reactions to clone CCSRP homologs. Probes based on the CCSRP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a CCSRP, such as by measuring a level of a CCSRP-encoding nucleic acid, in a sample of cells, e.g., detecting CCSRP mRNA levels or determining whether a genomic CCSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317–326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a CCSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89–108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CCSRPs, mutant forms of CCSRPs, fusion proteins, etc.).

The recombinant expression vectors of the invention can be designed for expression of CCSRPs in prokaryotic or eukaryotic cells. For example, CCSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423–488; van den Hondel, C. A. M. J. J. et al., 1991 Heterologous gene expression in filamentous fungi, in: More Gene Manipulations in Fungi, J. W. Bennet & L. L. Lasure, eds., p. 396–428: Academic Press: San Diego; and van den Hondel, C. A. M. J. J. & Punt, P. J., 1991 Gene transfer systems and vector development for filamentous fungi, in: Applied Molecular Genetics of Fungi, Peberdy, J. F. et al., eds., p. 1–28, Cambridge University Press: Cambridge), algae (Falciatore et al., 1999 Marine Biotechnology 1(3): 239–251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella, and Stylonychia, especially of the genus *Stylonychia lemnae* with vectors following a transformation method as described in PCT Application No. WO 98/01572 and multicellular plant cells (see Schmidt, R. and Willmitzer, L., 1988 High efficiency *Agrobacterium tumefaciens*-mediated transformation of *Arabidopsis thaliana* leaf and cotyledon explants, Plant Cell Rep. 583–586); Plant Molecular Biology and Biotechnology, C Press, Boca Raton, Fla., chapter 6/7, S. 71–119 (1993); F. F. White, B. Jenes et al., Techniques for Gene Transfer, in: Transgenic Plants, Vol. 1, Engineering and Utilization, eds. Kung und R. Wu, 128–43, Academic Press: 1993; Potrykus, 1991 Annu. Rev. Plant Physiol. Plant Molec. Biol. 42:205–225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the CCSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant CCSRP unfused to GST can be recovered by cleavage of the fusion protein with thrombin.

Examples of suitable inducible non-fusion *E. coli* expression vectors include pTrc (Amann et al., 1988 Gene 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the sequence of the nucleic acid to be inserted into an expression vector so that the individual codons for each amino acid are those preferentially utilized in the bacterium chosen for expression, such as *C. glutamicum* (Wada et al., 1992 Nucleic Acids Res. 20:2111–2118). Such alteration of nucleic acid sequences of the invention can be carried out by standard DNA synthesis techniques.

In another embodiment, the CCSRP expression vector is a yeast expression vector. Examples of vectors for expression in yeast *S. cerevisiae* include pYepSec1 (Baldari, et al., 1987 EMBO J. 6:229–234), pMFa (Kujan and Herskowitz, 1982 Cell 30:933–943), pJRY88 (Schultz et al., 1987 Gene 54:113–123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1–28, Cambridge University Press: Cambridge.

Alternatively, the CCSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell Biol. 3:2156–2165) and the pVL series (Lucklow and Summers, 1989 Virology 170:31–39).

In yet another embodiment, a CCSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual.* $2^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268–277), lymphoid-specific promoters (Calame and Eaton, 1988 Adv. Immunol. 43:235–275), in particular promoters of T cell receptors (Winoto and Baltimore, 1989 EMBO J. 8:729–733) and immunoglobulins (Banerji et al., 1983 Cell 33:729–740; Queen and Baltimore, 1983 Cell 33:741–748), neuron-specific promoters (e.g., the neurofilament promoter; Byrne and Ruddle, 1989 PNAS 86:5473–5477), pancreas-specific promoters (Edlund et al., 1985 Science 230:912–916), and mammary gland-specific promoters (e.g., milk whey promoter; U.S. Pat. No. 4,873,316 and European Application Publication No. 264, 166). Developmentally regulated promoters are also encompassed, for example, the murine hox promoters (Kessel and Gruss, 1990 Science 249:374–379) and the fetoprotein promoter (Campes and Tilghman, 1989 Genes Dev. 3:537–546).

In another embodiment, the CCSRPs of the invention may be expressed in unicellular plant cells (such as algae) (see Falciatore et al., 1999 Marine Biotechnology 1(3):239–251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195–1197; and Bevan, M. W., 1984 Binary Agrobacterium vectors for plant transformation, Nucl. Acid. Res. 12:8711–8721; Vectors for Gene Transfer in Higher Plants; in: Transgenic Plants, Vol. 1, Engineering and Utilization, eds.: Kung and R. Wu, Academic Press, 1993, S. 15–38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693–8711).

Plant gene expression has to be operably linked to an appropriate promoter conferring gene expression in a timely, cell or tissue specific manner. Preferred are promoters driving constitutive expression (Benfey et al., 1989 EMBO J. 8:2195–2202) like those derived from plant viruses like the 35S CAMV (Franck et al., 1980 Cell 21:285–294), the 19S CaMV (see also U.S. Pat. No. 5,352,605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285–423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89–108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397–404) and an ethanol inducible promoter (PCT Application No. WO 93/21334).

Also, suitable promoters responding to biotic or abiotic stress conditions are those such as the pathogen inducible PRP1-gene promoter (Ward et al., 1993 Plant. Mol. Biol. 22:361–366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331–340).

Especially preferred are those promoters that confer gene expression in specific tissues and organs, such as guard cells and the root hair cells. Suitable promoters include the napin-gene promoter from rapeseed (U.S. Pat. No. 5,608, 152), the USP-promoter from Vicia faba (Baeumlein et al., 1991 Mol Gen Genet. 225(3):459–67), the oleosin-promoter from Arabidopsis (PCT Application No. WO 98/45461), the phaseolin-promoter from Phaseolus vulgaris (U.S. Pat. No. 5,504,200), the Bce4-promoter from Brassica (PCT Application No. WO 91/13980) or the legumin B4 promoter (LeB4; Baeumlein et al., 1992 Plant Journal, 2(2):233–9) as well as promoters conferring seed specific expression in monocot plants like maize, barley, wheat, rye, rice, etc. Suitable promoters to note are the 1pt2 or 1pt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, Sorghum kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from Arabidopsis described in PCT Application No. WO 99/46394.

The invention further provides a recombinant expression vector comprising a CCSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a CCSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1) 1986 and Mol et al., 1990 FEBS Letters 268:427–430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a CCSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, Agrobacterium protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, manihot, pepper, sunflower and tagetes, solanaceous plants like potato, tobacco, eggplant, and tomato, Vicia species, pea, alfalfa, bushy plants (coffee, cacao, tea), Salix species, trees (oil palm, coconut), perennial grasses and forage crops, these crop plants are also preferred target plants for a genetic engineering as one further embodiment of the present invention.

In particular, the invention provides a method of producing a transgenic plant with a CCSRP coding nucleic acid, wherein expression of the nucleic acid(s) in the plant results in increased tolerance to environmental stress as compared to a wild type variety of the plant comprising: (a) transforming a plant cell with an expression vector comprising a CCSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a CCSRP, comprising: (a) transforming the host cell with an expression vector comprising a CCSRP coding nucleic acid, and (b) expressing the CCSRP within the host cell, thereby increasing the expression of the gene transcribed in response to the CCSRP, as compared to a wild type variety of the host cell.

For such plant transformation, binary vectors such as pBinAR can be used (Höfgen and Willmitzer, 1990 Plant Science 66:221–230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4 (15):285–423). The signal peptide is cloned 5-prime in frame to the cDNA to archive subcellular localization of the fusion protein. Additionally, promoters that are responsive to abiotic stresses can be used with, such as the Arabidopsis promoter RD29A, the nucleic acid sequences disclosed herein. One skilled in the art will recognize that the promoter used should be operatively linked to the nucleic acid such that the promoter causes transcription of the nucleic acid which results in the synthesis of a mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or Agrobacterium mediated gene transfer. Agrobacterium mediated plant transformation can be performed using for example the GV3101(pMP90) (Koncz and Schell, 1986 Mol. Gen. Genet. 204:383–396) or LBA4404 (Clontech) *Agrobacterium tumefaciens* strain. Transformation can be performed by standard transformation and regeneration techniques (Deblaere et al., 1994 Nucl. Acids. Res. 13:4777–4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BT11-P ISBN 0-7923-2731-4; Glick, Bernard R.; Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238–242; De Block et al., 1989 Plant Physiol. 91:694–701). Use of antibiotica for Agrobacterium and plant selection depends on the binary vector and the Agrobacterium strain used for transformation. Rapeseed selection is normally performed using kanamycin as selectable plant marker. Agrobacterium mediated gene transfer to flax can be performed using, for example, a technique described by Mlynarova et al., 1994 Plant Cell Report 13:282–285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a CCSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a CCSRP gene into which a deletion, addition or substitution has been introduced to thereby alter, e.g., functionally disrupt, the CCSRP gene. Preferably, the CCSRP gene is a *Physcomitrella patens* CCSRP gene, but it can be a homolog from a related plant or even from a mammalian, yeast, or insect source. In a preferred embodiment, the vector is designed such that, upon homologous recombination, the endogenous CCSRP gene is functionally disrupted (i.e., no longer encodes a functional protein; also referred to as a knock-out vector). Alternatively, the vector can be designed such that, upon homologous recombination, the endogenous CCSRP gene is mutated or otherwise altered but still encodes a functional protein (e.g., the upstream regulatory region can be altered to thereby alter the expression of the endogenous CCSRP). To create a point mutation via homologous recombination, DNA-RNA hybrids can be used in a technique known as chimeraplasty (Cole-Strauss et al., 1999 Nucleic Acids Research 27(5):1323–1330 and Kmiec, 1999 Gene therapy American Scientist. 87(3):240–247). Homologous recombination procedures in *Physcomitrella patens* are also well known in the art and are contemplated for use herein.

Whereas in the homologous recombination vector, the altered portion of the CCSRP gene is flanked at its 5' and 3' ends by an additional nucleic acid molecule of the CCSRP gene to allow for homologous recombination to occur between the exogenous CCSRP gene carried by the vector and an endogenous CCSRP gene, in a microorganism or plant. The additional flanking CCSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368–4373 for cDNA based recombination in *Physcomitrella patens*). The vector is introduced into a microorganism or plant cell (e.g., via polyethylene glycol mediated DNA), and cells in which the introduced CCSRP gene has homologously recombined with the endogenous CCSRP gene are selected using art-known techniques.

In another embodiment, recombinant microorganisms can be produced that contain selected systems which allow for regulated expression of the introduced gene. For example, inclusion of a CCSRP gene on a vector placing it under control of the lac operon permits expression of the CCSRP gene only in the presence of IPTG. Such regulatory systems are well known in the art.

A host cell of the invention, such as a prokaryotic or eukaryotic host cell in culture, can be used to produce (i.e., express) a CCSRP. Accordingly, the invention further provides methods for producing CCSRPs using the host cells of the invention. In one embodiment, the method comprises culturing the host cell of invention (into which a recombinant expression vector encoding a CCSRP has been introduced, or into which genome has been introduced a gene encoding a wild-type or altered CCSRP) in a suitable medium until CCSRP is produced. In another embodiment, the method further comprises isolating CCSRPs from the medium or the host cell.

Another aspect of the invention pertains to isolated CCSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of CCSRP in which the protein is separated from some of the cellular components of the cells in which it is naturally or recombinantly produced. In one embodiment, the language "substantially free of cellular material" includes preparations of a CCSRP having less than about 30% (by dry weight) of non-CCSRP material (also referred to herein as a "contaminating protein"), more preferably less than about 20% of non-CCSRP material, still more preferably less than about 10% of non-CCSRP material, and most preferably less than about 5% non-CCSRP material.

When the CCSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of CCSRP in which the protein is separated from chemical precursors or other chemicals that are involved in the synthesis of the protein. In one embodiment, the language "substantially free of chemical precursors or other chemicals" includes preparations of a CCSRP having less than about 30% (by dry weight) of chemical precursors or non-CCSRP chemicals, more preferably less than about 20% chemical precursors or non-CCSRP chemicals, still more preferably less than about 10% chemical precursors or non-CCSRP chemicals, and most preferably less than about 5% chemical precursors or non-CCSRP chemicals. In preferred embodiments, isolated proteins, or biologically active portions thereof, lack contaminating proteins from the same organism from which the CCSRP is derived. Typically, such proteins are produced by recombinant expression of, for example, a *Physcomitrella patens* CCSRP in plants other than *Physcomitrella patens* or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Phy-* scomitrella patens; identification and localization of *Physcomitrella patens* sequences of interest; evolutionary studies; determination of CCSRP regions required for function; modulation of a CCSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like Ceratodon and Physcomitrella share a high degree of homology on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The CCSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a CCSRP nucleic acid, wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass and forage crops, for example.

In particular, the present invention describes using the expression of CC-1, CC-2 and CC-3 of *Physcomitrella patens* to engineer drought-tolerant, salt-tolerant and/or cold-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a CCSRP selected from CC-1 (SEQ ID NO:7), CC-2 (SEQ ID NO:8) and CC-3 (SEQ ID NO:9), wherein the environmental stress is drought, increased salt or decreased or increased temperature. In preferred embodiments, the environmental stress is drought or decreased temperature.

The present invention also provides methods of modifying stress tolerance of a plant comprising, modifying the expression of a CCSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a CCSRP in a plant.

The methods of increasing expression of CCSRPs can be used wherein the plant is either transgenic or not transgenic. In cases when the plant is transgenic, the plant can be transformed with a vector containing any of the above described CCSRP coding nucleic acids, or the plant can be transformed with a promoter that directs expression of native CCSRP in the plant, for example. The invention provides that such a promoter can be tissue specific. Furthermore, such a promoter can be developmentally regulated. Alternatively, non-transgenic plants can have native CCSRP expression modified by inducing a native promoter.

The expression of CC-1 (SEQ ID NO:7), CC-2 (SEQ ID NO:8) or CC-3 (SEQ ID NO:9) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the CC-1 (SEQ ID NO:7), CC-2 (SEQ ID NO:8) or CC-3 (SEQ ID NO:9) homologs in the target plant as well as from its promoter. Zinc-finger-containing recombinant transcription factors are engineered to specifically interact with the CC-1 (SEQ ID NO:7), CC-2 (SEQ ID NO:8) or CC-3 (SEQ ID NO:9) homolog and transcription of the corresponding gene is activated.

In addition to introducing the CCSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The CCSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the CCSRP nucleic acid molecules of the invention may result in the production of CCSRPs having functional differences from the wild-type CCSRPs. These proteins may be improved in efficiency or activity, may be present in greater numbers in the cell than is usual, or may be decreased in efficiency or activity.

There are a number of mechanisms by which the alteration of a CCSRP of the invention may directly affect stress response and/or stress tolerance. In the case of plants expressing CCSRPs, increased transport can lead to improved salt and/or solute partitioning within the plant tissue and organs. By either increasing the number or the activity of transporter molecules which export ionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469–714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1–27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as Arabidopsis, soy, rape, maize, wheat, *Medicago truncatula*, etc., using standard protocols. The resulting transgenic cells and/or plants derived there from can then be assayed for fail or alteration of their tolerance to drought, salt, and temperature stress.

The engineering of one or more CCSRP genes of the invention may also result in CCSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226–235). While these products are typically excreted, cells can be genetically altered to transport more products than is typical for a wild-type cell. By optimizing the activity of one or more CCSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39–48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246–252.

The aforementioned mutagenesis strategies for CCSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like *C. glutamicum* expressing mutated CCSRP nucleic acid and protein molecules such that the stress tolerance is improved.

The present invention also provides antibodies that specifically bind to a CCSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163–167; Bebbington et al., 1992 Bio/Technology 10:169–175).

The phrases "selectively binds" and "specifically binds" with the polypeptide refer to a binding reaction that is determinative of the presence of the protein in a heterogeneous population of proteins and other biologics. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1
Growth of Physcomitrella patens Cultures

For this study, plants of the species Physcomitrella patens (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438–446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromols$^{-1m2}$ (white light; Philips TL 65W/25 fluorescent tube) and a light/dark change of 16/8 hours. The moss was either modified in liquid culture using Knop medium according to Reski and Abel (1985, Planta 165:354–358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2
Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000× g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C. and the RNAse digestion was subsequently carried out at 37° C. for 1 hour. Storage of the DNA took place at 4° C.

Example 3
Isolation of Total RNA and Poly-(A)+ RNA and cDNA Library Construction from Physcomitrella patens For the investigation of transcripts, both total RNA and poly-(A)$^+$ RNA were isolated. The total RNA was obtained from wild-type 9 day old protonemata following the GTC-method (Reski et al. 1994, Mol. Gen. Genet., 244:352–359). The Poly(A)+ RNA was isolated using Dyna Beads$^R$ (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4
Sequencing and Function Annotation of Physcomitrella patens ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands. Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:
5'-CAGGAAACAGCTATGACC-3' SEQ ID NO:10
5'-CTAAAGGGAACAAAAGCTG-3' SEQ ID NO:11
5'-TGTAAAACGACGGCCAGT-3' SEQ ID NO:12

Sequences were processed and annotated using the software package EST-MAX commercially provided by Bio-Max (Munich, Germany). The program incorporates practically all bioinformatics methods important for functional and structural characterization of protein sequences. For reference the website at pedant.mips.biochem.mpgde. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63–98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403–10; PREDATOR: High-accuracy secondary structure prediction from single and multiple sequences. Frishman, D. and Argos, P. (1997) 75% accuracy in protein secondary structure prediction. Proteins, 27:329–335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673–4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182–192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221–226 (1984). Version 2 by Dr. K. Nakai; PROSEARCH: Detection of PROSITE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919–921; BLIMPS: Similarity searches against a database of ungapped blocks. J. C. Wallace and Henikoff S., (1992); PATMAT: A searching and extraction program for sequence, pattern and block queries and databases, CABIOS 8:249–254. Written by Bill Alford.

Example 5

Identification of *Physcomitrella patens* ORFs Corresponding to CC-1, CC-2 and CC-3

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: CC-1 (SEQ ID NO:1), CC-2 (SEQ ID NO:2) and CC-3 (SEQ ID NO:3).

TABLE 1

| Name | Functional categories | Function | Sequence code | ORF position |
|---|---|---|---|---|
| PpCC-1 | Cell Cycle | suppressor protein | c_pp004062017r | 116–886 |
| PpCC-2 | Cell Cycle | cell division control protein | c_pp004064149r | 1–590 |
| PpCC-3 | Cell Cycle | cell division proteins | s_pp002007053r | 106–492 |

TABLE 2

Degree of Amino Acid Identity and Similarity of PpCC-1 and Other Homologous Proteins GCG Gap program was used: gap penalty: 10; gap extension penalty: 0.1; score matrix: blosum62)

| Swiss-Prot # | Q9ZNT0 | P46467 | P52917 | Q9UI03 | Q09803 |
|---|---|---|---|---|---|
| Protein name | PUTATIVE SKD1 PROTEIN | SKD1 PROTEIN | VACUOLAR PROTEIN SORTING-ASSOCIATED PROTEIN VPS4 | SKD1 PROTEIN | SUPPRESSOR PROTEIN OF BEM1/BED5 DOUBLE MUTANTS |
| Species | *Arabidopsis thaliana* (Mouse-ear cress) | *Mus musculus* (Mouse) | *Saccharomyces cerevisiae* (Baker's yeast) | *Homo sapiens* (Human) | *Schizosaccharomyces pombe* (Fission yeast) |
| Identity % | 82% | 54% | 55% | 53% | 52% |
| Similarity % | 90% | 66% | 67% | 65% | 65% |

TABLE 3

Degree of Amino Acid Identity and Similarity of PpCC-2 and Other Homologous Proteins GCG Gap program was used: gap penalty: 10; gap extension penalty: 0.1; score matrix: blosum62)

| Swiss-Prot # | Q9SIV8 | P29458 | P30665 | P49717 | P33991 |
|---|---|---|---|---|---|
| Protein name | PUTATIVE CDC21 PROTEIN | CDC21 PROTEIN | CELL DIVISION CONTROL PROTEIN 54 | DNA REPLICATION LICENSING FACTOR MCM4 | DNA REPLICATION LICENSING FACTOR MCM4 |
| Species | *Arabidopsis thaliana* (Mouse-ear cress) | *Schizosacc haromyces pombe* (Fission yeast) | *Saccharomyces cerevisiae* (Baker's yeast) | *Mus musculus* (Mouse) | *Homo sapiens* (Human) |
| Identity % | 49% | 41% | 40% | 43% | 43% |
| Similarity % | 61% | 55% | 54% | 56% | 57% |

TABLE 4

Degree of Amino Acid Identity and Similarity of PpCC-3 and Other Homologous Proteins GCG Gap program was used: gap penalty: 10; gap extension penalty: 0.1; score matrix: blosum62)

| Swiss-Prot # | O80860 | Q9LXF7 | P51327 | O78516 | Q55700 |
|---|---|---|---|---|---|
| Protein name | PUTATIVE CELL DIVISION PROTEIN (ZINC DEPENDENT PROTEASE) | FTSH-LIKE PROTEIN PFTF | CELL DIVISION PROTEIN FTSH HOMOLOG | CELL DIVISION PROTEIN FTSH HOMOLOG | CELL DIVISION PROTEIN FTSH HOMOLOG 1 |
| Species | *Arabidopsis thaliana* (Mouse-ear cress) | *Arabidopsis thaliana* (Mouse-ear cress) | *Porphyra purpurea* | *Guillardia theta* (Cryptomonas phi) | Synechocyst is sp. (strain PCC 6803) |
| Identity % | 77% | 64% | 60% | 59% | 56% |
| Similarity % | 84% | 75% | 69% | 69% | 67% |

Example 6
Cloning of the full-length *Physcomitrella patens* cDNA Encoding for CC-1, CC-2 and CC-3

To isolate the clones encoding Pp CC-1 (SEQ ID NO:4), PpCC-2 (SEQ ID NO:5) and PpCC-3 (SEQ ID NO:6) from *Physcomitrella patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences CC-2 (SEQ ID NO:2) and CC-3 (SEQ ID NO:3) identified from the database search as described in Example 4 were used to design oligos for RACE (see Table 5). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of CC-2 and CC-3 and were used to design oligos for full-length cloning of the respective genes (see below full-length amplification).

Full-length Amplification

Full-length clones corresponding CC-1 (SEQ ID NO:4), CC-2 (SEQ ID NO:5), and CC-3 (SEQ ID NO:6) were obtained by performing polymerase chain reaction (PCR) with gene-specific primers (see Table 5) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indolyl-β-D-galactoside) and 0.8 mg IPTG (isopropylthio-β-D-galactoside) grown overnight at 37° C. White colonies were selected and used to inoculate 3 ml of liquid LB containing 100 μg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 5

Scheme and primers used for cloning of full-length clones

| Gene | Sites in final product | Isolation Method | Primers Race | Primer RT-PCR |
|---|---|---|---|---|
| PpCC-1 | EcoRV/ SacI | 5' RACE and RT-PCR for Full-length clone | N/A | RC409 (SEQ ID NO:13) GCGATATCGACC CAAGGTGTGTAG AGAAGGGGAT RC410 (SEQ ID NO:14) GCGAGCTCGCGA CTGATGCAACTCA CCCATGAA |
| PpCC-2 | AscI/ SacI | 5' Race and RT-PCR for Full-length clone | RC793: (SEQ ID NO:15) CCCAAATGCTT GGAGCCAGCGA CCT RC794: (SEQ ID NO:16) RC794: GACGTGCACGC AATCGATGTAG GTC NVT: (SEQ ID NO:17) AGTCGACCCCT GTCAGACTTCTT GA | RC990: (SEQ ID NO:18) ATGGCGCGCCGC ACTCACGTGAGG AATTGCACCTCC RC991: (SEQ ID NO:19) GCGAGCTCTGGG AATTGCGCATGG GAAACTGG |
| PpCC-3 | XmaI/ SacI | 5' RACE and RT-PCR for Full-length clone | NVT: (SEQ ID NO:20) CTGGCTACCCA AACCGCGTCGG AGA | RC695: (SEQ ID NO:21) ATCCCGGGTGAT ACGTTGTGCATAT TTGGTGTTGC RC696: (SEQ ID NO:22) GCGAGCTCTGAT ACAAGAGCGTCG ATGCTCCA |

Example 7
Engineering Stress-tolerant Arabidopsis Plants by Overexpressing the Genes CC-1, CC-2 and CC-3
Binary Vector Construction: Kanamycin The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the Arabidopsis Actin2 promoter with internal intron and the OCS3 terminator. Primers for PCR amplification of the NPTII gene were designed as follows:
5'NPT-Pst:
GCG-CTG-CAG-ATT-TCA-TTT-GGA-GAG-GAC-ACG (SEQ ID NO:23)
3'NPT-Fse:
CGC-GGC-CGG-CCT-CAG-AAG-AAC-TCG-TCA-AGA-AGG-CG (SEQ ID NO:24)

The 0.9 kilobase NPTII gene was amplified via PCR from pCambia 2301 plasmid DNA [94° C. 60 sec, {94° C. 60 sec, 61° C. (−0.1° C. per cycle) 60 sec, 72° C. 2 min}×25 cycles, 72° C. 10 min on Biometra T-Gradient machine], and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top10 cells (Invitrogen) and grown on LB plates with 50 ug/ml kanamycin sulfate overnight at 37° C. Colonies were then used to inoculate 2 ml LB media with 50 ug/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top10 cells (Invitrogen) under standard conditions, creating pBPSsc019 construct. Colonies were selected on LB plates with 50 μg/ml kanamycin sulfate and grown overnight at 37° C. These colonies were then used to inoculate 2 ml LB media with 50 μg/ml kanamycin sulfate and grown overnight at 37° C. Plasmid DNA was recovered using the Qiaprep Spin Miniprep kit (Qiagen) following the manufacturer's instructions.

The pBPSSCO19 construct was digested with KpnI and BsaI (Roche) according to manufacturer's instructions. The fragment was purified via agarose gel and then extracted via the Qiaex II DNA Extraction kit (Qiagen) as per its instructions, resulting in a 3 kilobase Act-NPT cassette, which included the Arabidopsis Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recircularized by self-ligating with T4 DNA Ligase (Roche), and transformed into Top 10 cells (Invitrogen) via standard conditions. Transformed cells were selected for on LB agar containing 50 μg/ml kanamycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacture's instructions. The recircularized plasmid was then digested with KpnI (Roche) and extracted from agarose gel via the Qiaex II DNA Extraction kit (Qiagen) as per manufacturers' instructions.

The Act-NPT Kpn-cut insert and the Kpn-cut pBPSJH001 recircularized vector were then ligated together using T4 DNA Ligase (Roche) and transformed into Top10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 μg/ml kanamycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propagated and recovered using the Plasmid Midiprep Kit (Qiagen) following the manufacturer's instructions.

Subcloning of CC-1, CC-2 and CC-3 into the Binary Vector

The fragments containing the different *Physcomitrella patens* transcription factors were subcloned from the recombinant PCR2.1 TOPO vectors by double digestion with restriction enzymes (see Table 6) according to manufacturer's instructions. The subsequence fragment was excised from agarose gel with a QIAquick Gel Extraction Kit (QIAgen) according to manufacture's instructions and ligated into the binary vectors pGMSG, cleaved with XmaI and Ecl136II and dephosphorylated prior to ligation. The resulting recombinant pGMSG contained the corresponding transcription factor in the sense orientation under the constitutive super promoter.

TABLE 6

Listed are the names of the various constructs of the *Physcomitrella patens* transcription factors used for plant transformation

| Gene | Enzymes used to generate gene fragment | Enzymes used to restrict pBPSJH001 | Binary Vector Construct |
| --- | --- | --- | --- |
| PpCC-1 | EcoRV/SacI | SmaI/SacI | pBPSSY032 |
| PpCC-2 | AscI/SacI | XmaI/SacI | pBPSsc335 |
| PpCC-3 | XmaI/SacI | XmaI/SacI | pBPSLVM186 |

Agrobacterium Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194–1199; Bent et al. 1994, Science 265:1856–1860).

Screening of Transformed Plants

T1 seeds were sterilized according to standard protocols (Xiong et al. 1999, Plant Molecular Biology Reporter 17: 159–170). Seeds were plated on ½ MS 0.6% agar supplemented with 1% sucrose, 50 $\mu$g/ml kanamycin (Sigma-Aldrich) and 2 $\mu$g/ml benomyl (Sigma-Aldrich). Seeds on plates were vernalized for four days at 4° C. The seeds were germinated in a climatic chamber at an air temperature of 22° C. and light intensity of 40 micromols$^{-1m2}$ (white light; Philips TL 65W/25 fluorescent tube) and 16 hours light and 8 hours dark day length cycle. Transformed seedlings were selected after 14 days and transferred to ½ MS 0.6% agar plates supplemented with 1% sucrose and allowed to recover for five-seven days.

Drought Tolerance Screening

T1 seedlings were transferred to dry, sterile filter paper in a petri dish and allowed to desiccate for two hours at 80% RH (relative humidity) in a Sanyo Growth Cabinet MLR-350H, micromols$^{-1m2}$ (white light; Philips TL 65W/25 fluorescent tube). The RH was then decreased to 60% and the seedlings were desiccated further for eight hours. Seedlings were then removed and placed on ½ MS 0.6% agar plates supplemented with 2 $\mu$g/ml benomyl and scored after five days.

Under drought stress conditions, PpCC-1 over-expressing *Arabidopsis thaliana* plants showed a 67% (6 survivors from 9 stressed plants) survival rate to the stress screening; PpCC-2, 75% (6 survivors from 8 stressed plants) and PpCC-3, 92% (11 survivors from 12 stressed plants), whereas the control only showed a 11% survival rate (1 survivor from 9 stressed plants) (see Table 7). It is noteworthy that the analyses of these transgenic lines were performed with T1 plants, and therefore, the results will be better when a homozygous, strong expresser is found.

TABLE 7

Summary of the drought stress tests

Drought Stress Test

| Gene Name | Number of survivors | Total number of plants | Percentage of survivors |
| --- | --- | --- | --- |
| PpCC-1 | 6 | 9 | 67% |
| PpCC-2 | 6 | 8 | 75% |
| PpCC-3 | 11 | 12 | 92% |

Freezing Tolerance Screening

Seedlings were moved to petri dishes containing ½ MS 0.6% agar supplemented with 2% sucrose and 2 $\mu$g/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing −1° C. hour. The seedlings were then incubated at −5.0° C. for 24 hours and then allowed to thaw at 5° C. for 12 hours. The water was poured off and the seedlings were scored after 5 days.

Under freezing stress conditions, PpCC-1 over-expressing *Arabidopsis thaliana* plants showed a 89% (8 survivors from 9 stressed plants) survival rate to the stress screening, whereas the untransformed control only showed a 2% survival rate (1 survivor from 48 stressed plants) (see Table 8). It is noteworthy that the analyses of these transgenic lines were performed with T1 plants, and therefore, the results will be better when a homozygous, strong expresser is found.

TABLE 8

Summary of the freezing stress tests

Freezing Stress Test

| Gene Name | Number of survivors | Total number of plants | Percentage of survivors |
| --- | --- | --- | --- |
| PpCC-1 | 8 | 9 | 89% |
| Control | 1 | 48 | 2% |

Salt Tolerance Screening

Seedlings were transferred to filter paper soaked in ½ MS and placed on ½ MS 0.6% agar supplemented with 2 $\mu$g/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing ½ MS 0.6% agar supplemented with 2 $\mu$g/ml benomyl. The seedlings were scored after 5 days.

The transgenic plants are screened for their improved salt tolerance demonstrating that transgene expression confers salt tolerance.

Example 8
Detection of the CC-1, CC-2 and CC-3 Transgenes in the Transgenic Arabidopsis Lines One leaf from a wild type and a transgenic Arabidopsis plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60–65° C. for 30 minutes and 250 µl of Chloroform was then added to each sample. The samples were vortexed for 3 minutes and centrifuged for 5 minutes at 18,000× g. The supernatant was taken from each sample and 150 µl isopropanol was added. The samples were incubated at room temperature for 15 minutes, and centrifuged for 10 minutes at 18,000× g. Each pellet was washed with 70% ethanol, dried, and resuspended in 20 µl TE. 4 µl of above suspension was used in a 20 µl PCR reaction using Taq DNA polymerase (Roche Molecular Biochemicals) according to the manufacturer's instructions. The primers used in the reactions were:

PpCC-1
GCTGACACGCCAAGCCTCGCTAGTC (SEQ ID NO:25)
GCGAGCTCGCGACTGATGCAACTCACCCATGAA (SEQ ID NO:26)

The PCR program was as following: 30 cycles of 1 minute at 94° C., 1 minute at 62° C. and 4 minutes at 72° C., followed by 10 minutes at 72° C. A 1.6 kb fragment was produced from the positive control and the transgenic plants.

PpCC-2
GCTGACACGCCAAGCCTCGCTAGTC (SEQ ID NO:25)
GCGAGCTCTGGGAATTGCGCATGGGAAACTGG (SEQ ID NO:27)

The primers were used in the first round of reactions with the following program: 30 cycles of 1 minute at 94° C., 1 minute at 62° C. and 4 minutes at 72° C., followed by 10 minutes at 72° C. A 3 kb fragment was generated from the positive control and the T1 transgenic plants.

PpCC-3
GCTGACACGCCAAGCCTCGCTAGTC (SEQ ID NO:25)
GCGAGCTCTGATACAAGAGCGTCGATGCTCCA (SEQ ID NO:28)

The PCR program was as following: 30 cycles of 1 minute at 94° C., 1 minute at 62° C. and 4 minutes at 72° C., followed by 10 minutes at 72° C. A 2.3 kb fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control that could be amplified by this method.

Example 9
Detection of the CC-1, CC-2 and CC-3 Transgene mRNA in Transgenic Arabidopsis Lines Transgene expression was detected using RT-PCR. Total RNA was isolated from stress-treated plants using a procedure adapted from (Verwoerd et al., 1989 NAR 17:2362). Leaf samples (50–100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000× g. The upper aqueous phase was removed to a fresh eppendorf tube. RNA was precipitated by adding 1/10th volume 3M sodium acetate and 2 volumes 95% ethanol. Samples were mixed by inversion and placed on ice for 30 minutes. RNA was pelleted by centrifugation at 12,000× g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations.

PCR amplification of a gene-specific fragment from the synthesized cDNA was performed using Taq DNA polymerase (Roche) and gene-specific primers (see below for primers) in the following reaction: 1× PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and strongly suggested that their gene product improved plant stress tolerance in the transgenic line. On the other hand, no expression of identical or very similar endogenous genes could be detected by this method. These results are in agreement with the data from Example 7. This greatly supports our statement that the observed stress tolerance is due to the introduced transgene.

The following primer combination was used in the above-described reactions.

PpCC-1:
GATGGTGATGGTGACAGCGAGGATC (SEQ ID NO:29)
CGACGTGAAGCCTCGCTCTCATTTCC (SEQ ID NO:30)

PpCC-2:
CGATCTCCTTCAAGGGAACCTAGTGCTG (SEQ ID NO:31)
GAGTTCACGCATGTGCACCGATGCT (SEQ BD NO:32)

PpCC-3:
CGTAGCGTCTTCCAGGATGTCCTAC (SEQ BD NO:33)
GCTTGGCCTCGTCTACTCCCGCAAC (SEQ BD NO:34)

Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

Example 10
Engineering Stress-tolerant Soybean Plants by Over-expressing the CC-1, CC-2 and CC-3 Gene The constructs pBPSSY032, pBPSsc335 and pBPSLVM186 were used to transform soybean as described below.

Seeds of soybean were surface sterilized with 70% ethanol for 4 minutes at room temperature with continuous shaking, followed by 20% (v/v) Clorox supplemented with 0.05% (v/v) Tween for 20 minutes with continuous shaking. Then, the seeds were rinsed 4 times with distilled water and placed on moistened sterile filter paper in a Petri dish at room temperature for 6 to 39 hours. The seed coats were peeled off, and cotyledons are detached from the embryo axis. The embryo axis was examined to make sure that the meristematic region is not damaged. The excised embryo axes were collected in a half-open sterile Petri dish and air-dried to a moisture content less than 20% (fresh weight) in a sealed Petri dish until further use.

Agrobacterium tumefaciens culture was prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture was pelleted at 7000 rpm for 7 minutes at room temperature, and resuspended in MS (Murashige and Skoog, 1962) medium supplemented with 100 $\mu$M acetosyringone. Bacteria cultures were incubated in this pre-induction medium for 2 hours at room temperature before use. The axis of soybean zygotic seed embryos at approximately 15% moisture content were imbibed for 2 hours at room temperature with the pre-induced Agrobacterium suspension culture. The embryos are removed from the imbibition culture and were transferred to Petri dishes containing solid MS medium supplemented with 2% sucrose and incubated for 2 days, in the dark at room temperature. Alternatively, the embryos were placed on top of moistened (liquid MS medium) sterile filter paper in a Petri dish and incubated under the same conditions described above. After this period, the embryos were transferred to either solid or liquid MS medium supplemented with 500 mg/L carbenicillin or 300 mg/L cefotaxime to kill the agrobacteria. The liquid medium was used to moisten the sterile filter paper. The embryos were incubated during 4 weeks at 25° C., under 150 $\mu$mol m$^{-2}$sec$^{-1}$ and 12 hours photoperiod. Once the seedlings produced roots, they were transferred to sterile metromix soil. The medium of the in vitro plants was washed off before transferring the plants to soil. The plants were kept under a plastic cover for 1 week to favor the acclimatization process. Then the plants were transferred to a growth room where they were incubated at 25° C., under 150 $\mu$mol m$^{-2}$sec$^{-1}$ light intensity and 12 hours photoperiod for about 80 days.

The transgenic plants were then screened for their improved drought, salt and/or cold tolerance according to the screening method described in Example 7 demonstrating that transgene expression confers stress tolerance.

Example 11
Engineering Stress-tolerant Rapeseed/Canola Plants by Over-expressing the CC-1, CC-2 and CC-3 genes The constructs pBPSSY032, pBPSsc335 and pBPSLVM186 were used to transform rapeseed/canola as described below.

The method of plant transformation described herein is also applicable to Brassica and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (T0) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 demonstrating that transgene expression confers drought tolerance.

Example 12
Engineering Stress-tolerant Corn Plants by Over-expressing the CC-1, CC-2 and CC-3 Genes The constructs pBPSSY032, pBPSsc335 and pBPSLVM186 were used to transform corn as described below.

Transformation of maize (Zea Mays L.) is performed with the method described by Ishida et al. 1996. Nature Biotch 14745–50. Immature embryos are co-cultivated with Agrobacterium tumefaciens that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 demonstrating that transgene expression confers stress tolerance.

Example 13
Engineering Stress-tolerant Wheat Plants by Over-expressing the CC-1, CC-2 and CC-3 Genes The constructs pBPSSY032, pBPSsc335 and pBPSLVM186 were used to transform wheat as described below.

Transformation of wheat is performed with the method described by Ishida et al. 1996 Nature Biotch. 14745–50. Immature embryos are co-cultivated with Agrobacterium tumefaciens that carry "super binary" vectors, and transgenic plants are recovered through organogenesis. This procedure provides a transformation efficiency between 2.5% and 20%. The transgenic plants are then screened for their improved stress tolerance according to the screening method described in Example 7 demonstrating that transgene expression confers drought tolerance.

Example 14
Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10–20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:
6×SSC
0.01 M sodium phosphate
1 mM EDTA (pH 8)
0.5% SDS
100 μg/ml denatured salmon sperm DNA
0.1% nonfat dried milk During hybridization, temperature is lowered stepwise to 5–10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15
Identification of Homologous Genes by Screening Expression Libraries with Antibodies c-DNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257–262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16
In vivo Mutagenesis

In vivo mutagenesis of microorganisms can be performed by passage of plasmid (or other vector) DNA through *E. coli* or other microorganisms (e.g. Bacillus spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and Salmonella, p. 2277–2294, ASM: Washington.) Such strains are well known to those skilled in the art. The use of such strains is illustrated, for example, in Greener, A. and Callahan, M. (1994) Strategies 7: 32–34. Transfer of mutated DNA molecules into plants is preferably done after selection and testing in microorganisms. Transgenic plants are generated according to various examples within the exemplification of this document.

Example 17
In vitro Analysis of the Function of Physcomitrella Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, 2nd ed. VCH: Weinheim (ISBN 3527300325); Bergrneyer, H. U., Bergmeyer, J., Graβ3l, M., eds. (1983–1986) Methods of Enzymatic Analysis, $3^{rd}$ ed., vol. I–XII, Verlag Chemie: Weinheim; and Ullmann's Encyclopedia of Industrial Chemistry (1987) vol. A9, Enzymes. VCH: Weinheim, p. 352–363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) EMBO J. 14: 3895–3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85–137, 199–234 and 270–322, Springer: Heidelberg (1989).

Example 18
Purification of the Desired Product from Transformed Organisms

Recovery of the desired product from plant material (i.e., *Physcomitrella patens* or *Arabidopsis thaliana*), fungi, algae, ciliates, *C. glutamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133–140; Malakhova et al., 1996 *Biotekhnologiya* 11:27–32; and Schmidt et al., 1998 *Bioprocess Engineer.* 19:67–70. Ulmann's Encyclopedia of Industrial Chemistry, (1996) vol. A27, VCH: Weinheim, p. 89–90, p. 521–540, p. 540–547, p. 559–566, 575–581 and p. 581–587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

We claim:

1. A transgenic plant cell transformed with a nucleic acid encoding a polypeptide, wherein the polypeptide is defined in SEQ ID NO:7.

2. The transgenic plant cell of claim 1, wherein the nucleic acid comprises the polynucleotide as defined in SEQ NO:4.

3. A transgenic plant cell transformed with a nucleic acid encoding a polypeptide, wherein expression of the polypeptide in the plant cell results in the plant cell's increased tolerance to an environmental stress selected from one or more of the group consisting of drought and temperature less than or equal to 0° C. as compared to an untransformed wild type variety of the plant cell; wherein the nucleic acid hybridizes under stringent conditions to at least one sequence selected from the group consisting of the sequence of SEQ ID NO:4 and the full-length complement of the sequence of SEQ ID NO:4; and wherein the stringent conditions comprise hybridization in a 6× sodium chloride/sodium citrate (6×SSC) solution at 65° C. and at least one wash in a 0.2×sodium chloride/sodium citrate (SSC), 0.1% SDS solution at 50° C.

4. A transgenic plant cell transformed with a nucleic acid encoding a polypeptide, having at least 90% sequence identity with a polypeptide as defined in SEQ ID NO:7, wherein expression of the polypeptide in the plant cell results in the plant cell's increased tolerance to an environmental stress selected from one or more of the group consisting of drought and temperature less than or equal to 0° C. as compared to an untransformed wild type variety of the plant cell.

5. The transgenic plant cell of any of claims 1, 2, 3, or 4, wherein the plant is a monocot.

6. The transgenic plant cell of any of claims 1, 2, 3, or 4, wherein the plant is a dicot.

7. The transgenic plant cell of any of claims 1, 2, 3, or 4, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, and perennial grass.

8. A transgenic plant comprising the plant cell according to any of claims 1, 2, 3, or 4.

9. A seed produced by a transgenic plant comprising the plant cell according to any of claims 1, 2, 3, or 4, wherein the seed comprises the nucleic acid encoding the polypeptide, wherein the seed is true breeding for an increased tolerance to an environmental stress as compared to an untransformed wild type variety of the plant cell, and wherein the environmental stress is selected from one or more of the group consisting of drought and temperature less than or equal to 0° C.

10. An isolated nucleic acid encoding a polypeptide, wherein the nucleic acid comprises a polynucleotide that encodes the polypeptide as defined in SEQ ID NO:7.

11. The isolated nucleic acid of claim 10, wherein the nucleic acid comprises the polynucleotide as defined in SEQ ID NO:4.

12. An isolated nucleic acid encoding a polypeptide, wherein expression of the polypeptide in the plant cell results in the plant cell's increased tolerance to an environmental stress selected from one or more of the group consisting of drought and temperature less than or equal to 0° C. as compared to an untransformed wild type variety of the plant cell; wherein the nucleic acid hybridizes under stringent conditions to at least one sequence selected from the group consisting of the sequence of SEQ ID NO:4 and the full-length complement of the sequence of SEQ ID NO:4; and wherein the stringent conditions comprise hybridization in a 6×sodium chloride/sodium citrate (6×SSC) solution at 65° C. and at least one wash in a 0.2× (SSC), 0.1% SDS solution at 50° C.

13. An isolated nucleic acid, encoding a polypeptide having at least 90% sequence identity with the polypeptide as defined in SEQ ID NO:7, wherein expression of the polypeptide in the plant cell results in the plant cell's increased tolerance to an environmental stress selected from one or more of the group consisting of drought and temperature less than or equal to 0° C., as compared to an untransformed wild type variety of the plant cell.

14. An isolated recombinant expression vector comprising the nucleic acid of any one of claims 10, 11, 12 or 13, wherein expression of the polypeptide in a plant cell results in the plant cell's increased tolerance to an environmental stress as compared to an untransformed wild type variety of the plant cell, and wherein the environmental stress is selected from one or more of the group consisting of drought and temperature less than or equal to 0° C.

15. A method of producing a transgenic plant comprising a nucleic acid encoding a polypeptide, comprising,
   a. transforming a plant cell with the expression vector of claim 14; and
   b. generating from the plant cell a transgenic plant that expresses the polypetide;
wherein the polypeptide is defined in SEQ ID NO:7.

16. The method of claim 15, wherein the expression vector comprises the polynucleotide as defined in SEQ ID NO:4.

17. A method of producing a transgenic plant comprising a nucleic acid encoding a polypeptide, wherein expression of the polypeptide in the plant results in the plant's increased tolerance to an environmental stress, as compared to a an untransformed wild type variety of the plant, comprising,
   a. transforming a plant cell with the expression vector of claim 14; and
   b. generating from the plant cell a transgenic plant that expresses the polypeptide;
wherein the nucleic acid hybridizes under stringent conditions to at least one sequence selected from the group consisting of the sequence of SEQ ID NO:4 and the full-length complement of the sequence of SEQ ID NO:4; wherein the stringent conditions comprise hybridization in a 6× sodium chloride/sodium citrate (6×SSC) solution at 65° C. and at least one wash in a 0.2× (SSC), 0.1% SDS solution at 50° C.; and wherein the environmental stress is selected from one or more of the group consisting of drought and temperature less than or equal to 0° C.

18. A method of producing a transgenic plant comprising a nucleic acid encoding a polypeptide, wherein expression of the polypeptide in the plant results in the plant's increased tolerance to an environmental stress, as compared to a an untransformed wild type variety of the plant, comprising,
   a. transforming a plant cell with the expression vector of claim 14; and
   b. generating from the plant cell a transgenic plant that expresses the polypeptide;
wherein the polypeptide has at least 90% sequence identity with the polypeptide as defined in SEQ ID NO:7, and wherein the environmental stress is selected from one or more of the group consisting of drought and temperature less than or equal to 0° C.

* * * * *

UNITED STATES PATENT AND TRADEMARK OFFICE
CERTIFICATE OF CORRECTION

PATENT NO. : 6,710,229 B2
DATED : March 23, 2004
INVENTOR(S) : Oswaldo da Costa e Silva et al.

It is certified that error appears in the above-identified patent and that said Letters Patent is hereby corrected as shown below:

<u>Title page,</u>
Item [75], Inventors, please delete "Rouying Chen" and insert -- Ruoying Chen --

Signed and Sealed this

Twenty-fifth Day of May, 2004

JON W. DUDAS
*Acting Director of the United States Patent and Trademark Office*